United States Patent
Sharkey et al.

(10) Patent No.: US 8,221,403 B2
(45) Date of Patent: *Jul. 17, 2012

(54) UTERINE THERAPY DEVICE AND METHOD

(75) Inventors: Hugh R. Sharkey, Redwood City, CA (US); Ramiro Reyes, Redwood City, CA (US); Kurt D. Sparks, Redwood City, CA (US)

(73) Assignee: Aegea Medical, Inc., Redwood City, CA (US)

( * ) Notice: Subject to any disclaimer, the term of this patent is extended or adjusted under 35 U.S.C. 154(b) by 930 days.

This patent is subject to a terminal disclaimer.

(21) Appl. No.: 12/197,111

(22) Filed: Aug. 22, 2008

(65) Prior Publication Data

US 2009/0054871 A1 Feb. 26, 2009

Related U.S. Application Data

(60) Provisional application No. 60/957,626, filed on Aug. 23, 2007.

(51) Int. Cl.
*A61B 18/04* (2006.01)
(52) U.S. Cl. .......................................................... 606/27
(58) Field of Classification Search ............... 606/20–26, 606/193, 27
See application file for complete search history.

(56) References Cited

U.S. PATENT DOCUMENTS

| | | |
|---|---|---|
| 3,924,628 A | 12/1975 | Droegemueller et al. |
| 4,976,711 A | 12/1990 | Parins et al. |
| 5,045,056 A | 9/1991 | Behl |
| 5,084,044 A | 1/1992 | Quint |
| 5,122,138 A | 6/1992 | Manwaring |
| 5,437,629 A | 8/1995 | Goldrath |
| 5,443,470 A | 8/1995 | Stern et al. |
| 5,449,380 A | 9/1995 | Chin |
| 5,451,208 A | 9/1995 | Goldrath |
| 5,540,658 A | 7/1996 | Evans et al. |
| 5,542,928 A | 8/1996 | Evans et al. |
| 5,674,191 A | 10/1997 | Edwards et al. |
| 5,683,366 A | 11/1997 | Eggers et al. |

(Continued)

FOREIGN PATENT DOCUMENTS

WO     WO 99/53853 A1     10/1999
(Continued)

OTHER PUBLICATIONS

Sharkey et al.; U.S. Appl. No. 12/197,096 entitled "Uterine therapy device and method," Aug. 22, 2008.

(Continued)

*Primary Examiner* — Christopher D Koharski
(74) *Attorney, Agent, or Firm* — Shay Glenn LLP

(57) ABSTRACT

A method and system of providing therapy to a patient's uterus. The system has an access tool with a lumen, the access tool being adapted to be inserted through a human cervical canal to place an opening of the lumen within a uterus when the access tool is inserted through the cervical canal; a seal disposed at a distal region of the access tool and adapted to seal the access tool against an interior cervical os; a sealing indicator adapted to provide a user with an indication that the seal has sealed the access tool with the interior cervical os; and a vapor delivery mechanism adapted to deliver condensable vapor through the access tool to the uterus, the condensable vapor being adapted to condense within the uterus.

9 Claims, 21 Drawing Sheets

U.S. PATENT DOCUMENTS

| | | | |
|---|---|---|---|
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,730,719 A | 3/1998 | Edwards | |
| 5,743,870 A | 4/1998 | Edwards | |
| 5,769,880 A | 6/1998 | Truckai et al. | |
| 5,800,379 A | 9/1998 | Edwards | |
| 5,810,764 A | 9/1998 | Eggers et al. | |
| 5,820,580 A | 10/1998 | Edwards et al. | |
| 5,836,906 A | 11/1998 | Edwards | |
| 5,843,019 A | 12/1998 | Eggers et al. | |
| 5,871,469 A | 2/1999 | Eggers et al. | |
| 5,873,855 A | 2/1999 | Eggers et al. | |
| 5,888,198 A | 3/1999 | Eggers et al. | |
| 5,891,095 A | 4/1999 | Eggers et al. | |
| 5,891,457 A | 4/1999 | Neuwirth | |
| 5,902,272 A | 5/1999 | Eggers et al. | |
| 6,015,406 A | 1/2000 | Goble et al. | |
| 6,024,733 A | 2/2000 | Eggers et al. | |
| 6,045,532 A | 4/2000 | Eggers et al. | |
| 6,045,549 A | 4/2000 | Smethers et al. | |
| 6,047,700 A | 4/2000 | Eggers et al. | |
| 6,053,172 A | 4/2000 | Hovda et al. | |
| 6,053,909 A | 4/2000 | Shadduck | |
| 6,063,079 A | 5/2000 | Hovda et al. | |
| 6,066,134 A | 5/2000 | Eggers et al. | |
| 6,086,585 A | 7/2000 | Hovda et al. | |
| 6,102,046 A | 8/2000 | Weinstein et al. | |
| 6,105,581 A | 8/2000 | Eggers et al. | |
| 6,109,268 A | 8/2000 | Thapliyal et al. | |
| 6,113,597 A | 9/2000 | Eggers et al. | |
| 6,117,109 A | 9/2000 | Eggers et al. | |
| 6,139,571 A | 10/2000 | Fuller et al. | |
| 6,149,620 A | 11/2000 | Baker et al. | |
| 6,159,194 A | 12/2000 | Eggers et al. | |
| 6,159,208 A | 12/2000 | Hovda et al. | |
| 6,179,824 B1 | 1/2001 | Eggers et al. | |
| 6,179,836 B1 | 1/2001 | Eggers et al. | |
| 6,183,469 B1 | 2/2001 | Thapliyal et al. | |
| 6,190,381 B1 | 2/2001 | Olsen et al. | |
| 6,203,542 B1 | 3/2001 | Ellsberry et al. | |
| 6,210,402 B1 | 4/2001 | Olsen et al. | |
| 6,210,404 B1 | 4/2001 | Shadduck | |
| 6,224,592 B1 | 5/2001 | Eggers et al. | |
| 6,228,078 B1 | 5/2001 | Eggers et al. | |
| 6,228,081 B1 | 5/2001 | Goble | |
| 6,228,082 B1 | 5/2001 | Baker et al. | |
| 6,235,020 B1 | 5/2001 | Cheng et al. | |
| 6,238,391 B1 | 5/2001 | Olsen et al. | |
| 6,254,600 B1 | 7/2001 | Willink et al. | |
| 6,261,286 B1 | 7/2001 | Goble et al. | |
| 6,264,650 B1 | 7/2001 | Hovda et al. | |
| 6,264,651 B1 | 7/2001 | Underwood et al. | |
| 6,264,652 B1 | 7/2001 | Eggers et al. | |
| 6,277,112 B1 | 8/2001 | Underwood et al. | |
| 6,277,114 B1 | 8/2001 | Bullivant et al. | |
| 6,283,961 B1 | 9/2001 | Underwood et al. | |
| 6,293,942 B1 | 9/2001 | Goble et al. | |
| 6,296,636 B1 | 10/2001 | Cheng et al. | |
| 6,296,638 B1 | 10/2001 | Davison et al. | |
| 6,306,129 B1 | 10/2001 | Little et al. | |
| 6,306,134 B1 | 10/2001 | Goble et al. | |
| 6,309,387 B1 | 10/2001 | Eggers et al. | |
| 6,312,408 B1 | 11/2001 | Eggers et al. | |
| 6,322,549 B1 | 11/2001 | Eggers et al. | |
| 6,355,032 B1 | 3/2002 | Hovda et al. | |
| 6,363,937 B1 | 4/2002 | Hovda et al. | |
| 6,364,877 B1 | 4/2002 | Goble et al. | |
| 6,379,351 B1 | 4/2002 | Thapliyal et al. | |
| 6,391,025 B1 | 5/2002 | Weinstein et al. | |
| 6,416,507 B1 | 7/2002 | Eggers et al. | |
| 6,416,508 B1 | 7/2002 | Eggers et al. | |
| 6,416,509 B1 | 7/2002 | Goble et al. | |
| 6,432,103 B1 | 8/2002 | Ellsberry et al. | |
| 6,461,350 B1 | 10/2002 | Underwood et al. | |
| 6,461,354 B1 | 10/2002 | Olsen et al. | |
| 6,464,695 B2 | 10/2002 | Hovda et al. | |
| 6,468,270 B1 | 10/2002 | Hovda et al. | |
| 6,468,274 B1 | 10/2002 | Alleyne et al. | |
| 6,482,201 B1 | 11/2002 | Olsen et al. | |
| 6,508,816 B2 | 1/2003 | Shadduck | |
| 6,510,854 B2 | 1/2003 | Goble | |
| 6,540,741 B1 | 4/2003 | Underwood et al. | |
| 6,544,261 B2 | 4/2003 | Ellsberry et al. | |
| 6,551,271 B2 | 4/2003 | Nguyen | |
| 6,557,559 B1 | 5/2003 | Eggers et al. | |
| 6,575,968 B1 | 6/2003 | Eggers et al. | |
| 6,582,423 B1 | 6/2003 | Thapliyal et al. | |
| 6,589,237 B2 | 7/2003 | Woloszko et al. | |
| 6,595,990 B1 | 7/2003 | Weinstein et al. | |
| 6,602,248 B1 | 8/2003 | Sharps et al. | |
| 6,620,155 B2 | 9/2003 | Underwood et al. | |
| 6,629,974 B2 | 10/2003 | Penny et al. | |
| 6,632,193 B1 | 10/2003 | Davison et al. | |
| 6,632,220 B1 | 10/2003 | Eggers et al. | |
| 6,669,694 B2 | 12/2003 | Shadduck | |
| 6,708,056 B2 | 3/2004 | Duchon et al. | |
| 6,712,811 B2 | 3/2004 | Underwood et al. | |
| 6,719,754 B2 | 4/2004 | Underwood et al. | |
| 6,726,684 B1 | 4/2004 | Woloszko et al. | |
| 6,746,447 B2 | 6/2004 | Davison et al. | |
| 6,749,604 B1 | 6/2004 | Eggers et al. | |
| 6,763,836 B2 | 7/2004 | Tasto et al. | |
| 6,766,202 B2 | 7/2004 | Underwood et al. | |
| 6,770,071 B2 | 8/2004 | Woloszko et al. | |
| 6,772,012 B2 | 8/2004 | Ricart et al. | |
| 6,773,431 B2 | 8/2004 | Eggers et al. | |
| 6,780,180 B1 | 8/2004 | Goble et al. | |
| 6,805,130 B2 | 10/2004 | Tasto et al. | |
| 6,832,996 B2 | 12/2004 | Woloszko et al. | |
| 6,837,887 B2 | 1/2005 | Woloszko et al. | |
| 6,837,888 B2 | 1/2005 | Ciarrocca et al. | |
| 6,896,672 B1 | 5/2005 | Eggers et al. | |
| 6,896,674 B1 | 5/2005 | Woloszko et al. | |
| 6,911,028 B2 | 6/2005 | Shadduck | |
| 6,915,806 B2 | 7/2005 | Pacek et al. | |
| 6,929,640 B1 | 8/2005 | Underwood et al. | |
| 6,929,642 B2 | 8/2005 | Xiao et al. | |
| 6,949,096 B2 | 9/2005 | Davison et al. | |
| 6,960,204 B2 | 11/2005 | Eggers et al. | |
| 6,991,631 B2 | 1/2006 | Woloszko et al. | |
| 7,004,940 B2 | 2/2006 | Ryan et al. | |
| 7,004,941 B2 | 2/2006 | Tvinnereim et al. | |
| 7,094,215 B2 | 8/2006 | Davison et al. | |
| 7,101,367 B2 | 9/2006 | Xiao et al. | |
| 7,104,986 B2 | 9/2006 | Hovda et al. | |
| 7,105,007 B2 | 9/2006 | Hibler | |
| RE3,935 E | 10/2006 | Goble | |
| 7,131,969 B1 | 11/2006 | Hovda et al. | |
| 7,169,143 B2 | 1/2007 | Eggers et al. | |
| 7,179,255 B2 | 2/2007 | Lettice et al. | |
| 7,186,234 B2 | 3/2007 | Dahla et al. | |
| 7,192,428 B2 | 3/2007 | Eggers et al. | |
| 7,201,750 B1 | 4/2007 | Eggers et al. | |
| 7,217,268 B2 | 5/2007 | Eggers et al. | |
| 7,241,293 B2 | 7/2007 | Davison | |
| 7,270,658 B2 | 9/2007 | Woloszko et al. | |
| 7,270,659 B2 | 9/2007 | Ricart et al. | |
| 7,270,661 B2 | 9/2007 | Dahla et al. | |
| 7,276,063 B2 | 10/2007 | Davison et al. | |
| 7,297,143 B2 | 11/2007 | Woloszko et al. | |
| 7,297,145 B2 | 11/2007 | Woloszko et al. | |
| 7,320,325 B2 | 1/2008 | Duchon et al. | |
| 2002/0013601 A1* | 1/2002 | Nobles et al. | 606/193 |
| 2002/0019627 A1 | 2/2002 | Maguire et al. | |
| 2002/0177846 A1* | 11/2002 | Mulier et al. | 606/27 |
| 2004/0068306 A1 | 4/2004 | Shadduck | |
| 2004/0199226 A1 | 10/2004 | Shadduck | |
| 2005/0177147 A1 | 8/2005 | Vancelette et al. | |
| 2006/0135955 A1 | 6/2006 | Shadduck | |
| 2006/0161233 A1 | 7/2006 | Barry et al. | |
| 2006/0224154 A1 | 10/2006 | Shadduck et al. | |
| 2007/0225744 A1 | 9/2007 | Nobles et al. | |
| 2007/0239197 A1 | 10/2007 | Dubey et al. | |
| 2008/0132826 A1 | 6/2008 | Shadduck et al. | |
| 2009/0125010 A1 | 5/2009 | Sharkey et al. | |

FOREIGN PATENT DOCUMENTS

| | | |
|---|---|---|
| WO | WO 00/29055 A1 | 5/2000 |
| WO | WO 03/070302 A1 | 8/2003 |
| WO | WO 2006/055695 A1 | 5/2006 |
| WO | WO 2006/108974 A1 | 10/2006 |

OTHER PUBLICATIONS

Sharkey et al.; U.S. Appl. 12/197,096 entitled "Uterine therapy device and method," filed Aug. 22, 2008.

Sharkey et al.; U.S. Appl. No. 12/197,104 entitled "Uterine therapy device and method," filed Aug. 22, 2008.

Van De Velde; Vapo-cauterization of the uterus; Amer. J. Med. Sci.; vol. CXVII; 1899.

Blacker; Vaporization of the uterus; J. Obstet. & Gyn.; pp. 488-511; 1901.

Neuwirth et al.; The endometrial ablator: a new instrument; Obst. & Gyn.; vol. 83; No. 5; part 1; pp. 792-796; 1994.

Prior et al.; Treatment of mennorrhagia by radiofrequency heating; Int. J. Hyperthermia; vol. 7; No. 2; pp. 213-220; 1991.

\* cited by examiner

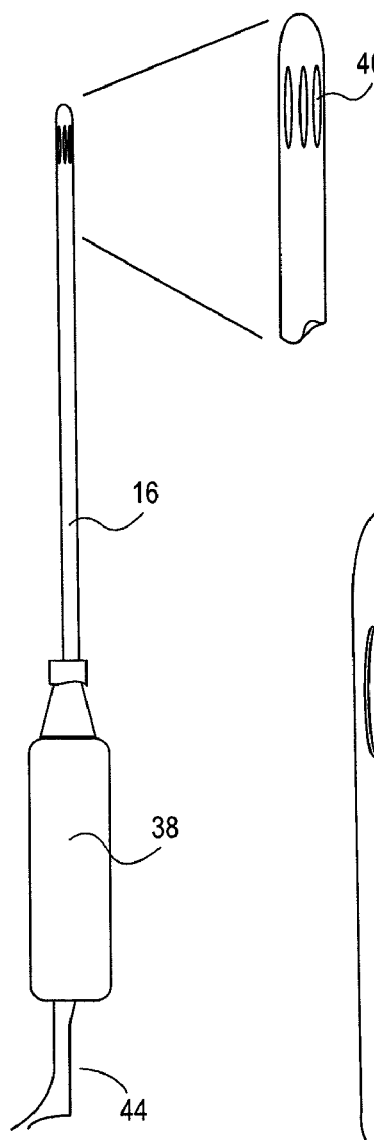
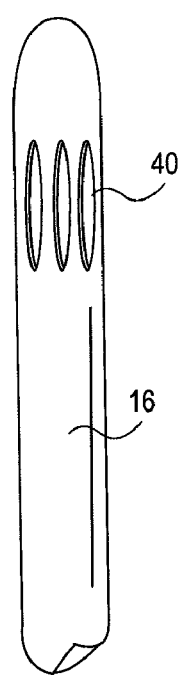
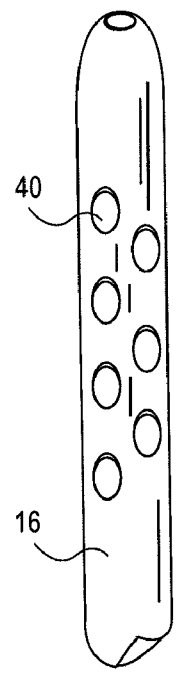
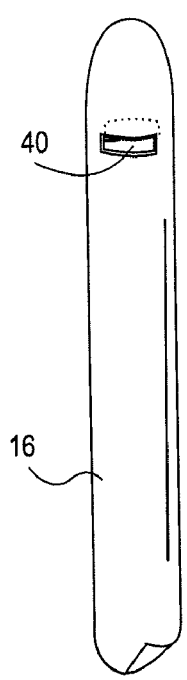
FIG. 4  FIG. 5  FIG. 6  FIG. 7

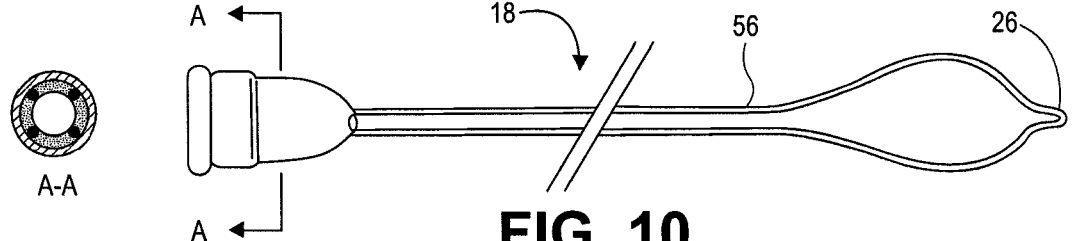
FIG. 11    FIG. 10
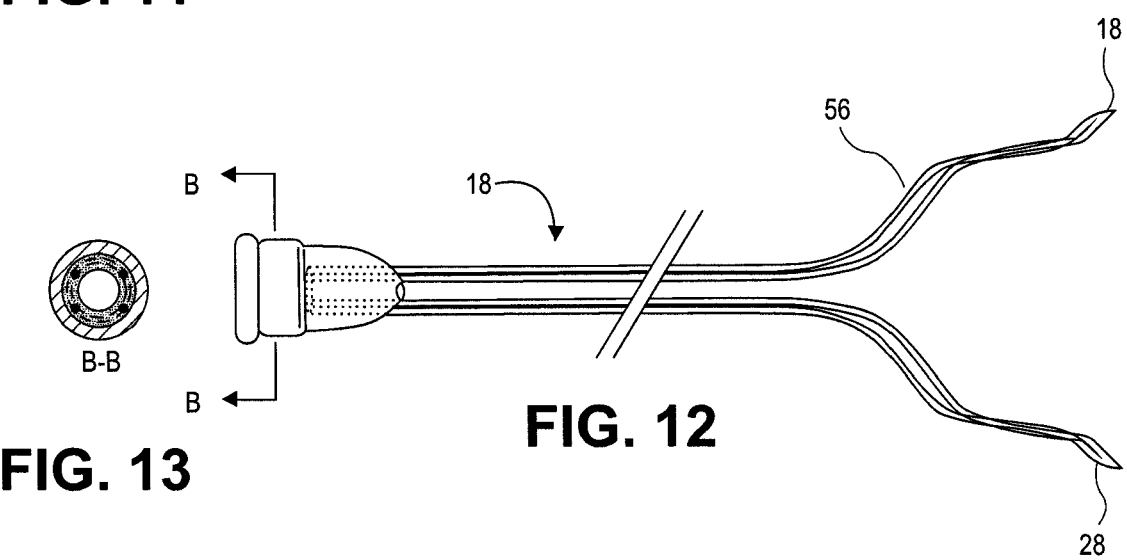
FIG. 13    FIG. 12
FIG. 14
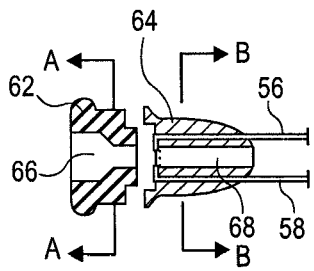 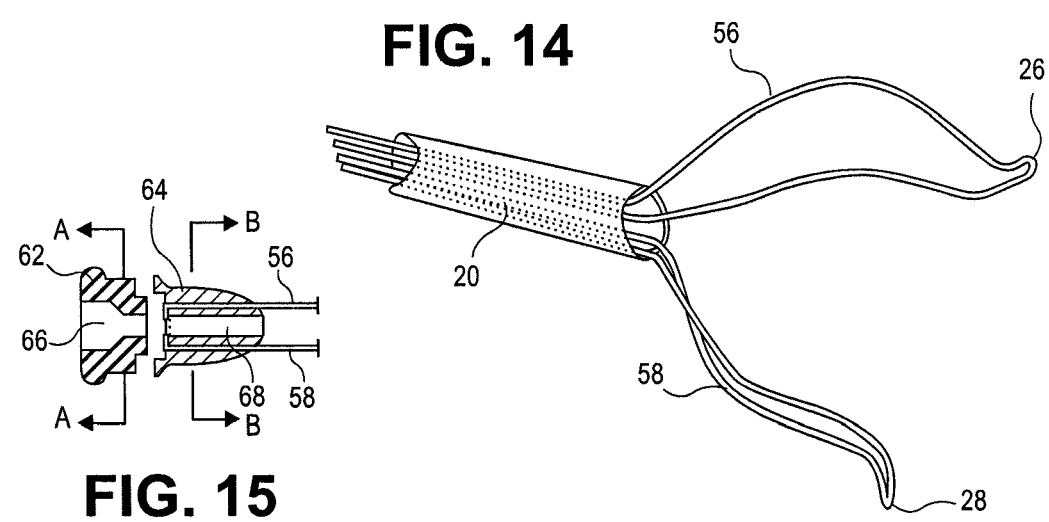
FIG. 15

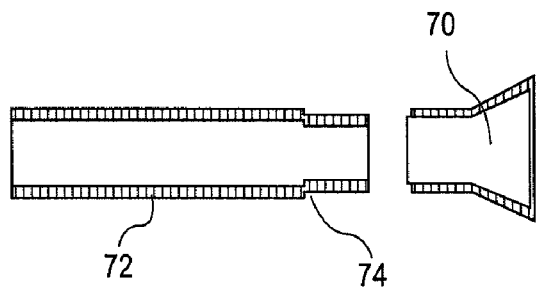
FIG. 16
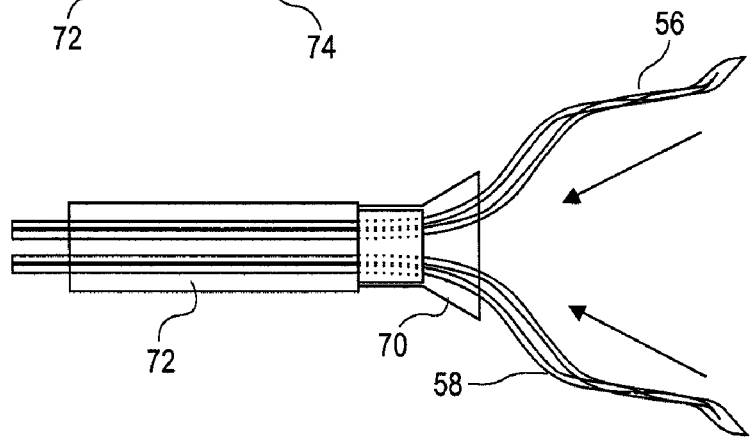
FIG. 17
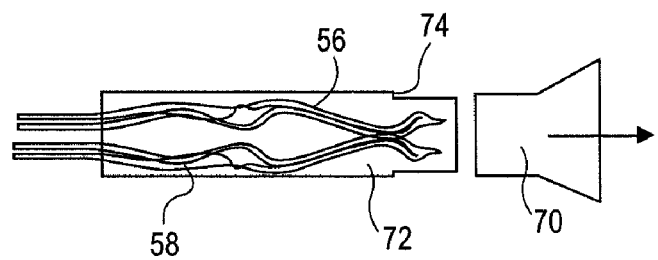
FIG. 18
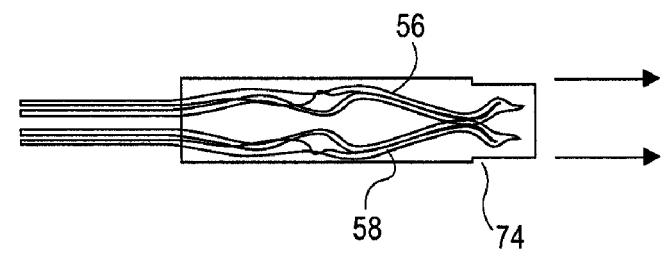
FIG. 19
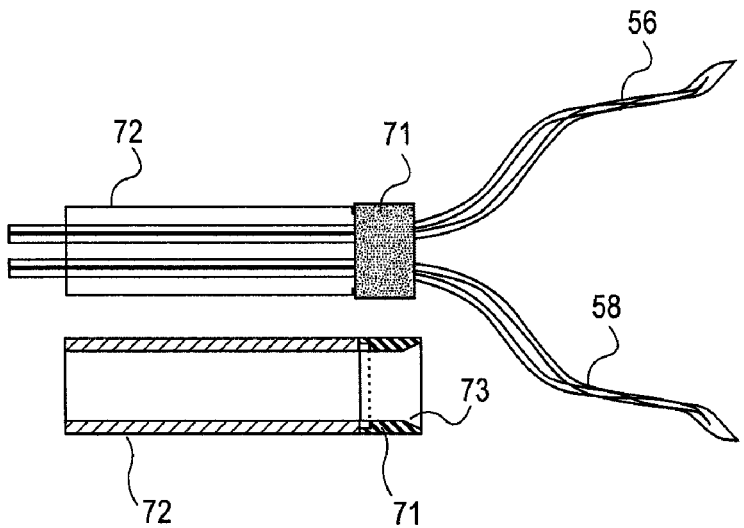
FIG. 20A
FIG. 20B

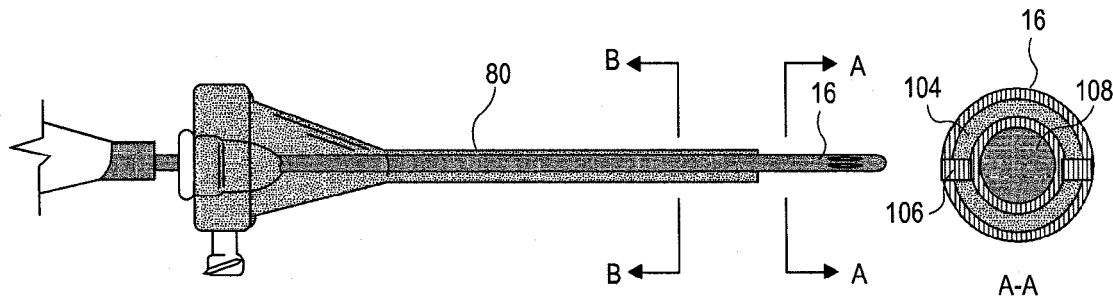
FIG. 41  FIG. 42
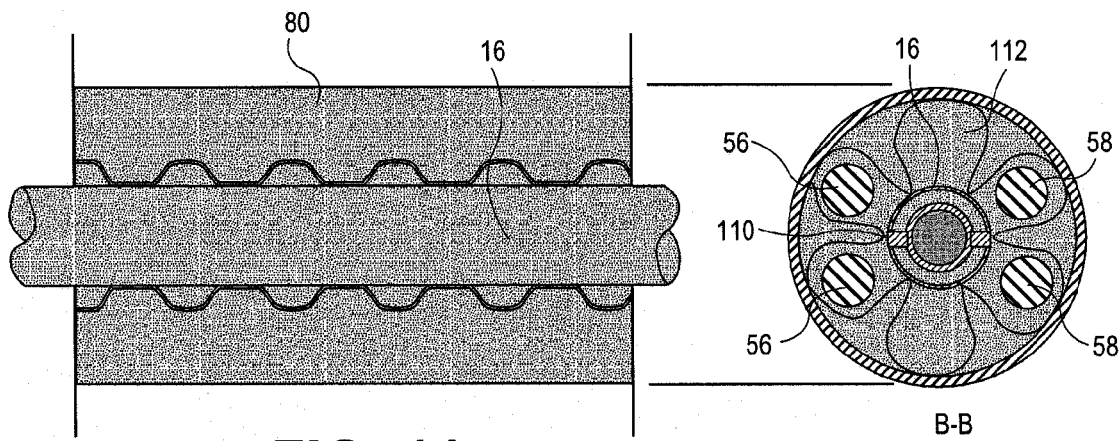
FIG. 44  FIG. 43
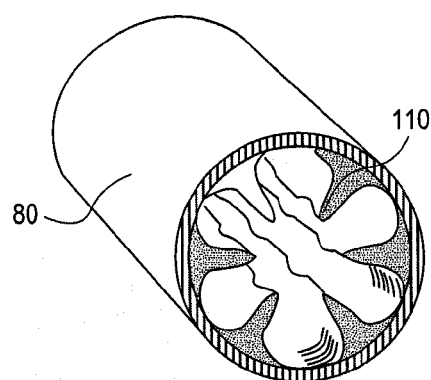
FIG. 45

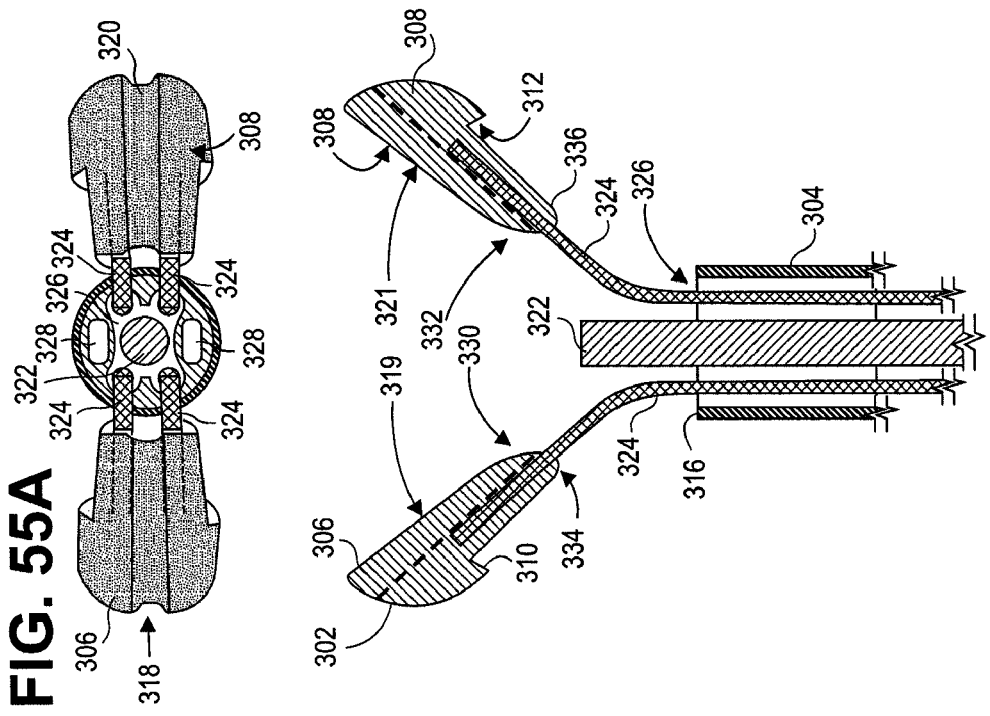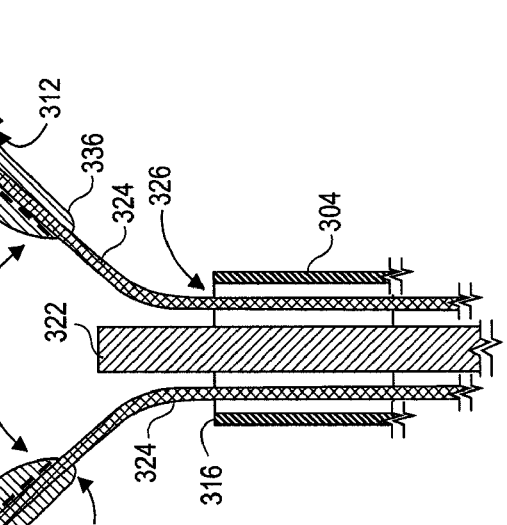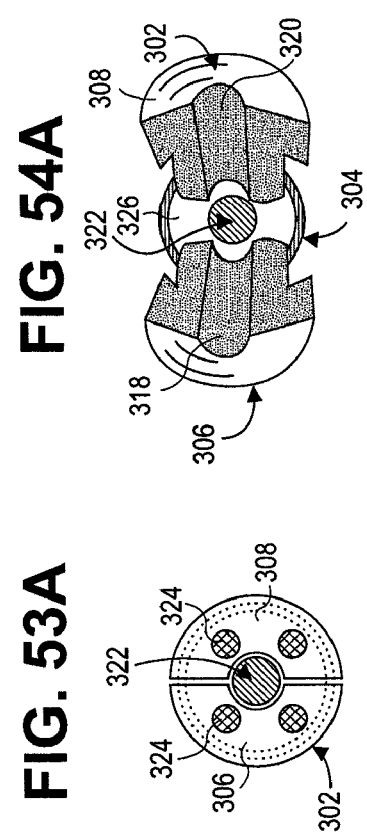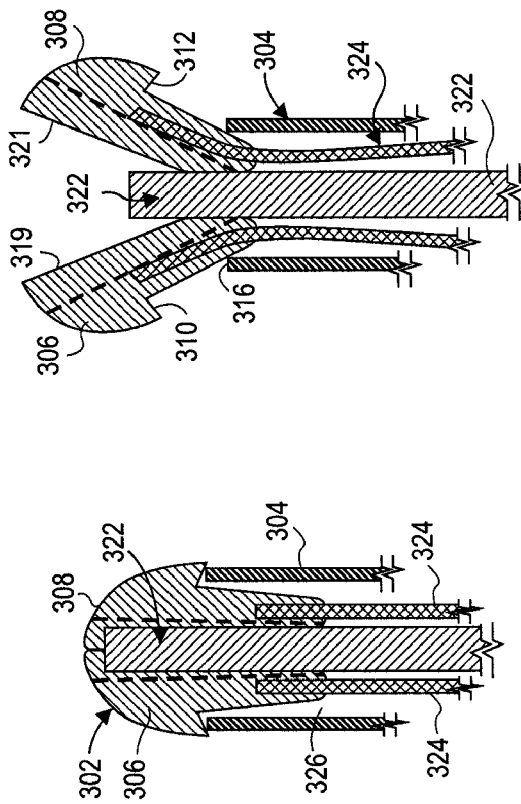

UTERINE THERAPY DEVICE AND METHOD

CROSS REFERENCE TO RELATED APPLICATIONS

This application claims the benefit under 35 U.S.C. §119 of U.S. Provisional Application No. 60/957,626, filed Aug. 23, 2007, the disclosure of which is incorporated by reference as if fully set forth herein.

This application is related to U.S. application Ser. No. 12/197,084, filed Aug. 22, 2008, entitled "Uterine Therapy Device and Method"; and to U.S. application Ser. No. 12/197,096, filed Aug. 22, 2008, entitled "Uterine Therapy Device and Method"; and to U.S. application Ser. No. 12/197,104, filed Aug. 22, 2008, entitled "Uterine Therapy Device and Method", all of which are commonly owned.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Endometrial ablation (i.e., the removal or destruction of the endometrial lining of the uterus) is used as an alternative to hysterectomy for treating menorrhagia, or other uterine diseases. One prior technique for performing endometrial ablation employ a resectoscope (i.e., a hysteroscope with a built-in wire loop or other ablative devices) that is inserted transcervically into the uterus, and uses radio-frequency electrical current (RF current) to remove or coagulate the endometrial tissue. These standard techniques typically are performed in a hospital setting.

Some approaches make use of heated fluid to ablate the endometrium. For example, early journal articles describe the use of steam to treat uterine hemorrhage. See, e.g., Van de Velde, "Vapo-"Cauterization of the Uterus," Amer. J. Med. Sci., vol. CXVIII (1899); Blacker, "Vaporization of the Uterus," J. Obstet. & Gyn., pp. 488-511 (c. 1901). The use of steam for this purpose was later discredited, apparently due to patient morbidity and mortality. See, e.g., Fuller U.S. Pat. No. 6,139,571. More recent descriptions of the use of injecting hot fluid into the uterus may be found in Goldrath U.S. Pat. No. 5,451,208 and Evans et al. U.S. Pat. No. 5,540,658; U.S. Pat. No. 5,437,629.

Uterine therapies employing a contained fluid have also been described. See, e.g., Quint U.S. Pat. No. 5,084,044; Chin U.S. Pat. No. 5,449,380; Neuwirth et al., "The Endometrial Ablator: A New Instrument", Obst. & Gyn., 1994, Vol. 83, No. 5, Part 1, pp 792-796. Another balloon-based system using ultrasound as the energy source is described in U.S. Pat. No. 7,004,940.

High frequency, or radiofrequency (RF), energy has been used to perform thermal ablation of endometrial tissue. See, e.g., Prior et al., "Treatment of Mennorrhagia By Radiofrequency Heating", Int. J. Hyperthermia, 1991 Vol. 7, No. 2, pp. 213-220; Stern et al. U.S. Pat. No. 5,443,470; U.S. Pat. No. 5,769,880; U.S. Pat. No. 6,929,642.

Current products for performing endometrial ablation include the NovaSure® procedure and a system marketed under the trade name THERMACHOICE®, by Ethicon, Inc. of Somerville, N.J.

Cryogenic ablation, or "cryoablation," is another endometrial treatment approach. See, e.g., Droegemueller et al. U.S. Pat. No. 3,924,628; U.S. Pat. No. 6,306,129; and U.S. Pat. No. 7,101,367.

Finally, U.S. Pat. Appl. Publ. No. 2004/0068306 describes the use of vapor, such as steam, for endometrial or other tissue ablation, and U.S. Pat. Appl. Publ. No. 2002/0177846 describes the use of vapor for treating uterine fibroids.

SUMMARY OF THE INVENTION

One aspect of the invention provides a method of providing therapy to a patient's uterus. The method includes the steps of inserting an access tool through a cervix and a cervical canal into the uterus; actively cooling the cervical canal; delivering vapor through the access tool lumen into the uterus; and condensing the vapor on tissue within the uterus. In some embodiments, the step of actively cooling comprising supplying a flow of coolant through a coolant flowpath in the access tool. The access tool may have an expandable member (such as, e.g., a balloon), in which case the coolant flowpath may be disposed within the expandable member, and the expandable member may be expanded with the coolant. The coolant flowpath may also have a coolant inlet communicating with a coolant source and a coolant outlet communicating with an interior volume of the expandable member, in which case the supplying step may include the step of supplying coolant flow from the coolant inlet through the coolant outlet. The coolant flowpath may also be a coolant lumen formed in the access tool, in which case the supplying step may include the step of supplying coolant flow from the coolant inlet through the coolant lumen.

In some embodiments, the method also includes the step of sealing an interior cervical os after the inserting step, e.g., by expanding an expandable member such as a balloon. The expanding step may also include the step of preferentially expanding a sealing portion of the balloon disposed at the interior cervical os prior to expanding an indicator portion of the balloon disposed proximal to the interior cervical os. The balloon may be expanded with coolant.

Some embodiments of the invention include the step of placing an expansion mechanism in contact with tissue within the uterus to move uterine tissue away from an opening in the lumen. The method may also include the step of advancing the expansion mechanism distally prior to the placing step.

In some embodiments, the step of delivering vapor includes the step of inserting a vapor delivery tool through the access tool lumen. The method may also include the step of exhausting vapor and vapor condensate from the uterus.

Another aspect of the invention provides a uterine heat therapy system including: an access tool with a lumen, the access tool being adapted to be inserted through a human cervical canal to place an opening of the lumen within a uterus when the access tool is inserted through the cervical canal; an active cooling mechanism adapted to cool the cervical canal, the active cooling mechanism having a coolant source; and a vapor delivery mechanism adapted to deliver condensable vapor through the access tool to the uterus, the condensable vapor being adapted to condense within the uterus. The access tool may have further a coolant flowpath communicating with the coolant source. The access tool may also have an expandable member (such as a balloon), with the coolant flowpath being disposed within the expandable member. The coolant flowpath may include a coolant inlet communicating with the coolant source and a coolant outlet communicating with an interior volume of the expandable member. The coolant flowpath may also be a coolant lumen formed in the access tool.

In some embodiments, the system has a seal disposed at a distal region of the access tool and adapted to seal against an interior cervical os. The seal may be, e.g., an expandable member, such as a balloon. The balloon may have a distal sealing portion adapted to preferentially expand prior to a proximal indicator portion when the balloon is expanded with fluid.

Some embodiments of the system also have an expansion mechanism adapted to contact tissue within the uterus to move uterine tissue away from the opening in the access tool lumen. Such a system may also have an advancement mechanism operatively connected to the expansion mechanism to move the expansion mechanism distally with respect to the access tool.

Some embodiments may also provide a vapor delivery tool adapted to be inserted through the access tool lumen.

Still another aspect of the invention provides a method of providing heat therapy to a patient's uterus. In some embodiments the method includes the steps of: inserting an access tool through a cervix and a cervical canal into the uterus; placing an expansion mechanism in contact with tissue within the uterus to move uterine tissue surfaces away from an opening in an access tool lumen; delivering vapor through the vapor delivery tool into the uterus; and condensing the vapor on tissue within the uterus.

In some embodiments, the method includes the step of advancing the expansion mechanism distally prior to the placing step. In some embodiments the expansion mechanism may be advanced to place a distal portion of the advancement mechanism adjacent a fallopian os prior to delivering vapor, and in some embodiments advancement of the expansion mechanism will cease before a distal portion of the advancement mechanism reaches a fallopian os and prior to delivery of vapor. Advancement of the expansion mechanism may be performed by moving an expansion mechanism actuator on the access tool.

In some embodiments the expansion mechanism may have two expansion arms, in which case the placing step may include the step of moving the expansion arms apart. In some embodiments distal portions of the expansion arms together form an obturator tip prior to the step of moving the expansion arms apart.

Some embodiments of the invention include the step of sealing an interior cervical os after the inserting step. In some embodiments, the step of delivering vapor includes the step of inserting a vapor delivery tool through the access tool lumen.

Yet another aspect of the invention provides a uterine heat therapy system including: an access tool adapted to be inserted through a human cervical canal to place an opening of an access tool lumen within a uterus when the access tool is inserted through the cervical canal; an expansion mechanism adapted to be advanced into the uterus to move uterine tissue surfaces away from the opening in the access tool lumen; and a vapor delivery mechanism adapted to deliver condensable vapor through the access tool to the uterus, the condensable vapor being adapted to condense within the uterus.

In some embodiments, the expansion mechanism, when fully advanced, is adapted to extend beyond the opening of the access tool lumen less than a distance from an interior cervical os of the uterus to a fallopian tube os of the uterus. In other embodiments the expansion mechanism, when fully advanced, is adapted to extend beyond the opening of the access tool lumen substantially all a distance from an interior cervical os of the uterus to a fallopian tube os of the uterus.

In some embodiments, the access tool includes an expansion mechanism actuator operatively connected to the expansion tool to expand the expansion tool. The expansion mechanism actuator may also be further adapted to advance the expansion mechanism distally beyond the opening of the access tool lumen.

In some embodiments, the expansion mechanism includes two expansion arms adapted to move apart as the expansion mechanism is advanced beyond the opening of the access tool lumen. In some of these embodiments, distal portions of the expansion arms together form an obturator tip prior to moving the expansion arms apart. In addition, each of the distal portions of the expansion arms is sized to substantially occlude a fallopian os of the uterus.

Some embodiments also include a seal disposed at a distal region of the access tool and adapted to seal against an interior cervical os. Some embodiments of the system also include a vapor delivery tool adapted to be inserted through the access tool lumen.

Still another aspect of the invention provides a method of providing heat therapy to a patient's uterus including the following steps: inserting an access tool through a cervix and a cervical canal into the uterus; after inserting the access tool into the uterus, inserting a vapor delivery tool through an access tool lumen; delivering vapor through the vapor delivery tool into the uterus; and condensing the vapor on tissue within the uterus.

Some embodiments of the invention also include the step of connecting the vapor delivery tool to a vapor source prior to the step of inserting the vapor delivery tool through the access tool lumen. In some of those embodiments, the method also includes the step of passing vapor from the vapor source through at least a portion of the vapor delivery tool to an exhaust port exterior the patient prior to delivering vapor to the uterus. In embodiments in which the vapor delivery tool has a vapor delivery actuator operatively connected to the vapor source, the method may further include the step actuating the vapor delivery actuator prior to the step of delivering vapor.

In some embodiments, the delivering step includes the step of delivering vapor through a plurality of exit ports in the vapor delivery tool, such as through an exit port disposed at a distal tip of the vapor delivery tool and through an exit port on a longitudinal portion of the vapor delivery tool. The delivering step may also further include the step of moving a movable member disposed within a vapor delivery tool lumen adjacent at least one exit port to alter vapor flow through the at least one exit port.

Some embodiments of the invention include the step of exhausting vapor and/or vapor condensate from the uterus, such as through a vapor exhaust channel disposed radially outward from a vapor delivery channel; through a vapor exhaust channel disposed between an exterior surface of the vapor delivery tool and an interior surface of the access tool; and/or through a vapor exhaust channel disposed in the vapor delivery tool. The method may also include the step of sealing an interior cervical os after the inserting step.

In some embodiments, the method includes the step of placing an expansion mechanism in contact with tissue within the uterus to move uterine tissue away from an opening in the lumen prior to the delivering step. The method may also include the step of advancing the expansion mechanism distally with respect to the access tool lumen prior to the placing step.

Another aspect of the invention provides a uterine heat therapy system including: an access tool, the access tool being adapted to be inserted through a human cervical canal to place an opening of the access tool lumen within a uterus when the access tool is inserted through the cervical canal;

and a vapor delivery mechanism, the vapor delivery mechanism having a vapor delivery tool and a vapor source, the vapor delivery tool being adapted to be inserted through the access tool to deliver condensable vapor from the vapor source to the uterus, the condensable vapor being adapted to condense within the uterus.

Some embodiments of the vapor delivery tool have a vapor exit port, in which case the vapor delivery mechanism may further have a vapor delivery tool warming circuit with a vapor flow path from the vapor source to a vapor exhaust without passing through the vapor delivery tool vapor exit port. In such embodiments, the vapor delivery mechanism may also have a vapor delivery tool connector, with the vapor delivery mechanism being configured to deliver vapor through the warming circuit automatically when the vapor delivery tool connector is connected to the vapor source. The vapor delivery mechanism may also have a vapor delivery actuator operatively connected to the vapor delivery tool and the vapor source to control delivery of vapor from the vapor source to a vapor delivery tool exit port and to direct vapor through the vapor delivery tool warming circuit.

Some embodiments of the vapor delivery tool have a plurality of vapor exit ports. In some of such embodiments, none of the vapor exit ports is at a distal tip of the vapor delivery tool. In some such embodiments, the plurality of exit ports include one or more exit ports on a longitudinal portion of the vapor delivery tool proximal to a distal tip of the vapor delivery tool. The vapor delivery tool may also include a movable member disposed within a vapor delivery tool lumen adjacent at least one exit port, the movable member being adapted to alter vapor flow through the at least one exit port in response to vapor flow through the vapor delivery tool.

In some embodiments, the vapor delivery tool has a vapor delivery channel, with the uterine heat therapy system further including a vapor exhaust channel adapted to exhaust vapor and/or condensed vapor from the uterus. The vapor delivery channel may be disposed radially inward from the vapor exhaust channel. In some embodiments, the vapor exhaust channel may be disposed between an exterior surface of the vapor delivery tool and an interior surface of the access tool. In some embodiments, the vapor exhaust channel may be disposed in the vapor delivery tool.

In some embodiments, the vapor delivery tool has an exit port at a distal end of a vapor delivery channel and an atraumatic tip disposed distal to the exit port. The vapor delivery tool may also have a flexible support (such as a coil) supporting the atraumatic tip. The flexible support may surround the exit port and may have a vapor passage.

In some embodiments, the vapor delivery tool has a vapor exhaust channel disposed radially outward from the vapor delivery channel. The vapor exhaust channel may have an inlet disposed proximal to the vapor delivery channel exit port.

Some embodiments of the invention have a seal disposed at a distal region of the access tool and adapted to seal against an interior cervical os. Some embodiments also have an expansion mechanism adapted to contact tissue within the uterus when the opening of the access tool is inserted into the uterus to move uterine tissue away from the opening in the access tool lumen.

Still another aspect of the invention provides a method of providing heat therapy to a patient's uterus, including the following steps: inserting an access tool through a cervix and a cervical canal into the uterus; after inserting the access tool into the uterus, creating a seal between an exterior surface of the access tool and an interior cervical os; providing an indication to a user that the seal has been created; delivering vapor through the access tool lumen into the uterus; and condensing the vapor on tissue within the uterus.

In some embodiments, the step of creating a seal comprises expanding an expandable member, such as a balloon. The expanding step may include the step of preferentially expanding a sealing portion of the balloon disposed at the interior cervical os prior to an indicator portion of the balloon disposed proximal to the interior cervical os. The expanding step may also include the step of supplying coolant to the balloon.

In some embodiments, the method includes the step of placing an expansion mechanism in contact with tissue within the uterus to move uterine tissue away from an opening in the access tool lumen. Some such embodiments include the step of advancing the expansion mechanism distally with respect to the access tool lumen prior to the placing step.

In some embodiments, the step of delivering vapor includes the step of inserting a vapor delivery tool through the access tool lumen. Some embodiments also include the step of exhausting vapor and/or vapor condensate from the uterus.

Yet another aspect of the invention provides a uterine heat therapy system having: an access tool with a lumen, the access tool being adapted to be inserted through a human cervical canal to place an opening of the lumen within a uterus when the access tool is inserted through the cervical canal; a seal disposed at a distal region of the access tool and adapted to seal the access tool against an interior cervical os; a sealing indicator adapted to provide a user with an indication that the seal has sealed the access tool with the interior cervical os; and a vapor delivery mechanism adapted to deliver condensable vapor through the access tool to the uterus, the condensable vapor being adapted to condense within the uterus.

In some embodiments, the seal includes an expandable member, such as a balloon. In some such embodiments, the balloon has a distal sealing portion adapted to preferentially expand prior to a proximal indicator portion when the balloon is expanded with fluid.

Some embodiments also include an expansion mechanism adapted to contact tissue within the uterus to move uterine tissue away from the opening in the access tool lumen. Some such embodiments also include an advancement mechanism operatively connected to the expansion mechanism to move the expansion mechanism distally with respect to the access tool. Some embodiments also include a vapor delivery tool adapted to be inserted through the access tool lumen.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 is an elevational view of a vapor delivery tool according to one embodiment of the invention along with a blow-up view of the tip of the vapor delivery tool.

FIG. 5 is an elevational view of a distal end of a vapor delivery tool according to another embodiment of the invention.

FIG. 6 is an elevational view of a distal end of a vapor delivery tool according to yet another embodiment of the invention.

FIG. 7 is an elevational view of a distal end of a vapor delivery tool according to still another embodiment of the invention.

FIG. 10 is an elevational view of an expansion mechanism of a uterine access tool according to one embodiment of the invention.

FIG. 11 is a cross-sectional view along the line A-A of the embodiment of FIG. 10.

FIG. 12 is another elevational view of the expansion mechanism of FIG. 10.

FIG. 13 is a cross-sectional view along the line B-B of the embodiment of FIG. 12.

FIG. 14 is a perspective view of the expansion mechanism of FIG. 10 emerging from a delivery tool cannula.

FIG. 15 is a cross-sectional view of portions of the embodiment of FIG. 10.

FIG. 16 is a cross-sectional view showing an expansion mechanism loading tool according to one embodiment of the invention.

FIGS. 17 and 18 are elevational views of the expansion mechanism loading tool of FIG. 16 in use.

FIG. 19 shows an expansion mechanism loaded into a uterine access tool according to one aspect of the invention.

FIG. 20A shows another embodiment of an expansion mechanism and uterine access tool.

FIG. 20B is a cross-sectional view of portions of the uterine access tool of FIG. 20A.

FIG. 41 shows still another embodiment of a uterine access tool and vapor delivery tool.

FIG. 42 is a cross-sectional view along the line A-A of the embodiment of FIG. 41.

FIG. 43 is a cross-sectional view along the line B-B of the embodiment of FIG. 41.

FIG. 44 is a partial view of yet another embodiment of the invention.

FIG. 45 is a partial cross-sectional view of the embodiment of FIG. 44.

FIG. 53A is an end elevational view of another uterine access tool embodiment.

FIG. 53B is a cross-sectional view of the uterine access tool of FIG. 53A.

FIG. 54A is an end elevational view of the uterine access tool of FIG. 53A showing the expansion mechanism partially advanced.

FIG. 54B is a cross-sectional view of the uterine access tool of FIG. 53A showing the expansion mechanism partially advanced.

FIG. 55A is an end elevational view of the uterine access tool of FIG. 53A showing the expansion mechanism fully advanced.

FIG. 55B is a cross-sectional view of the uterine access tool of FIG. 53A showing the expansion mechanism fully advanced.

DETAILED DESCRIPTION OF THE INVENTION

The present invention provides improved methods and apparatus for endometrial ablation using heated vapor.

Figure 1:
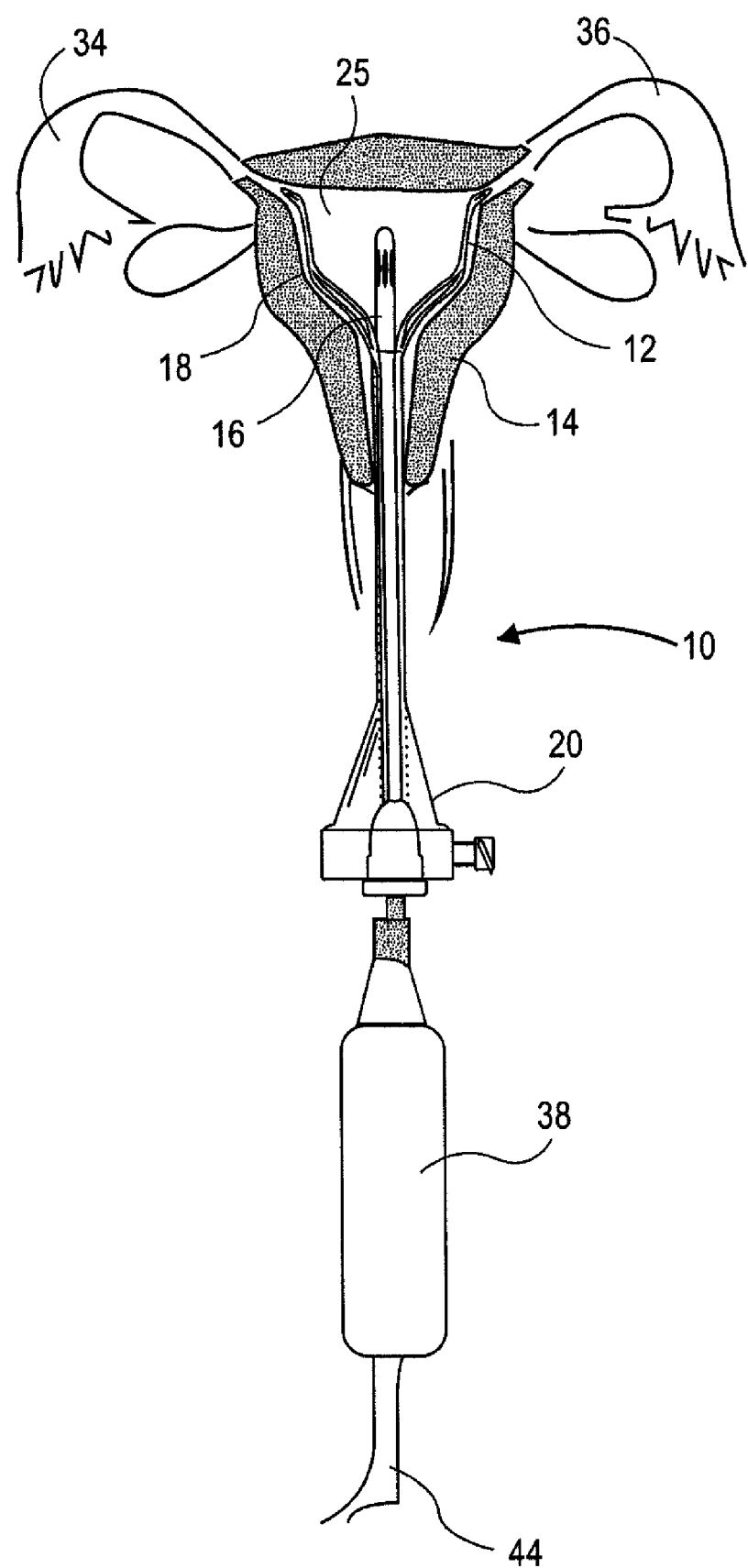
FIG. 1 is a partial cross-sectional drawing showing an embodiment of the invention in place in a uterus.
Figure 2:
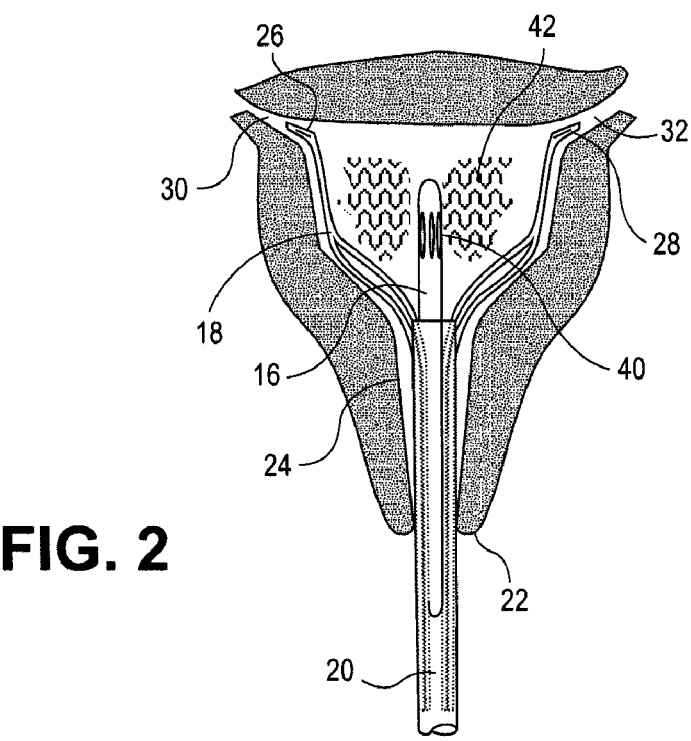
FIGS. 2 and 3 are partial cross-sectional drawings showing the embodiment of FIG. 1 treating a uterus.
Figure 3:
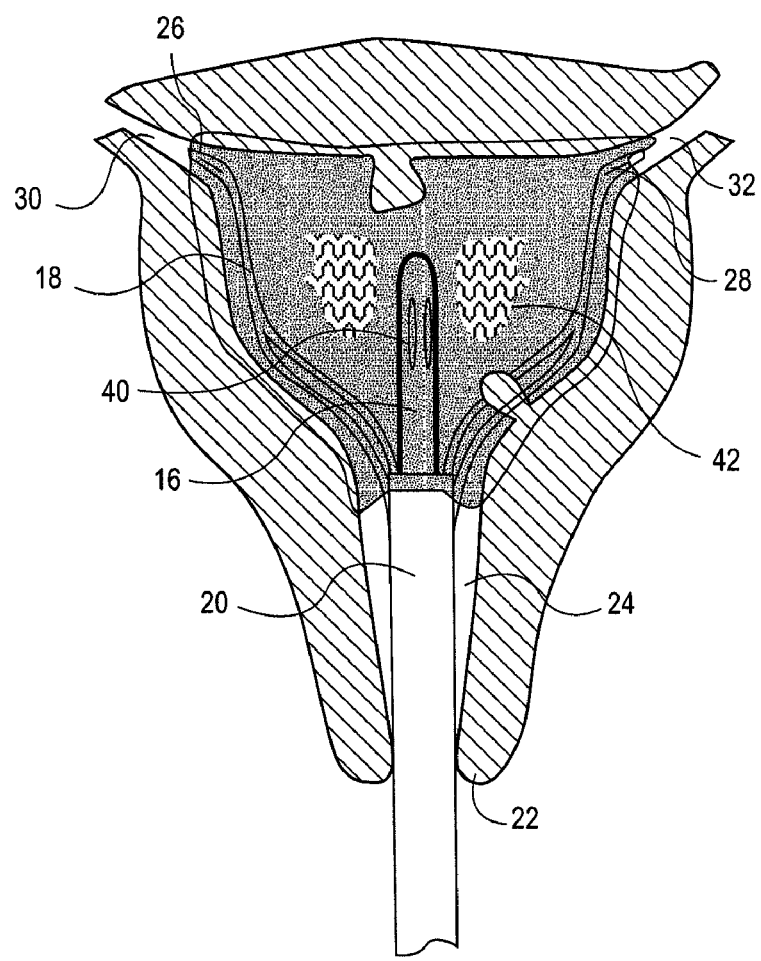

FIGS. 1-45 show embodiments of a system 10 for heating and ablating the endometrium 12 of a uterus 14. In these embodiments, the system 10 includes a vapor delivery component or tool 16, a uterus expansion mechanism, such as basket 18, and an access tool or introducer 20. As shown in FIGS. 1-3, basket 18 and the distal end of the vapor delivery component 16 have been inserted through the cervical os 22 and cervical canal 24 into the lumen or cavity 25 of the uterus. Basket 18 has been expanded after insertion to open up the uterine cavity and to keep tissue away from the vapor outlets of the vapor delivery component. The distal ends 26 and 28 of basket 18 are disposed in the os 30 and 32 of the Fallopian tubes 34 and 36 to orient the device within the cavity and to help seal the Fallopian tube os. The basket struts 56 and 58 conform to any irregularities in the uterine wall as shown in FIG. 3.

Vapor (such as steam) is produced in a handle portion 38 of vapor delivery component 16 or produced remotely by a vapor generator connected via a conduit, and introduced into the uterine cavity through ports 40 in the distal end of the vapor delivery component. Water may be supplied to handle 40 via water line 44. The steam within the uterine cavity is shown at 42. Further details of suitable vapor generation parameters and equipment may be found in US 2004/0068306.

FIGS. 6 and 7 show alternative shapes for vapor delivery component ports 40. In FIG. 6, ports 40 are round. In FIG. 7, ports 40 are slots.

Figures 8A, 8B, 9:
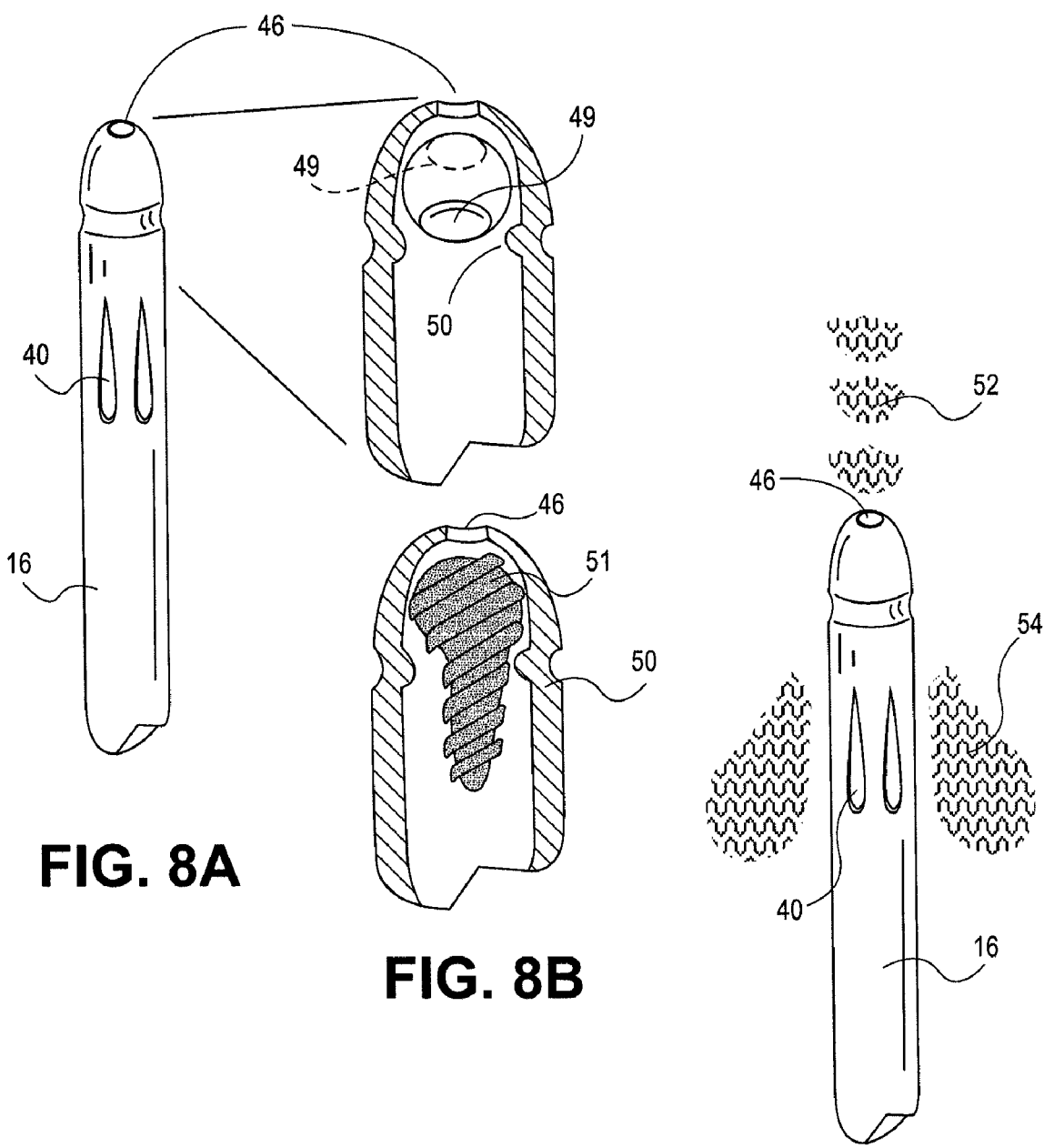
FIG. 8A is an elevational view of a distal end of a vapor delivery tool according to another embodiment of the invention along with a blow-up cross-sectional view.
FIG. 8B is a cross-sectional view of a distal end of a vapor delivery tool according to yet another embodiment of the invention.
FIG. 9 is an elevational view of the vapor delivery tool of FIG. 8A or 8B delivering vapor.
Figure 21A:
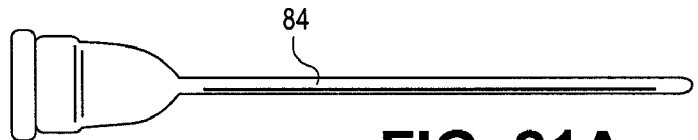
FIG. 21A is an elevational view of an obturator of a uterine access tool according to one embodiment of the invention.
Figure 21B:
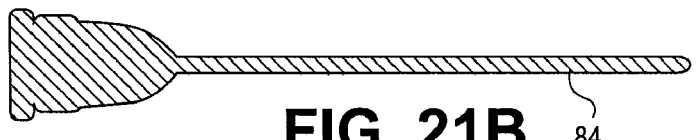
FIG. 21B is a cross-sectional view of the obturator of FIG. 21A.
Figure 22:
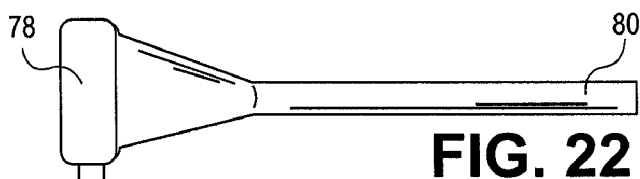
FIG. 22 is an elevational view of portions of a uterine access tool.
Figure 23:
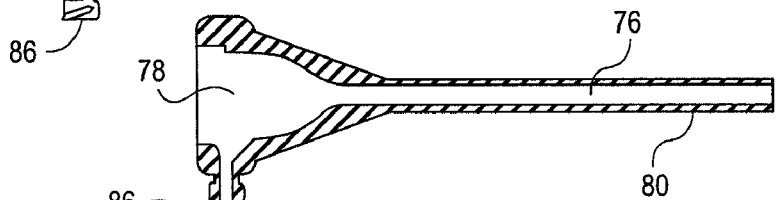
FIG. 23 is a cross-sectional view of the uterine access tool of FIG. 22.
Figure 24:
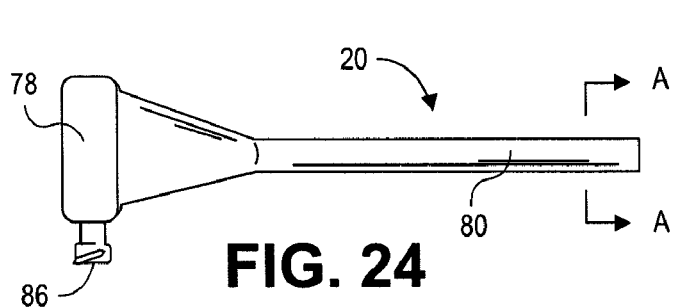
FIG. 24 is another elevational view of the access tool of FIG. 22.
Figure 25:
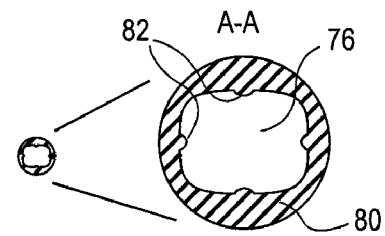
FIG. 25 is a cross-sectional view of the access tool along the line A-A of FIG. 24.
Figure 26:
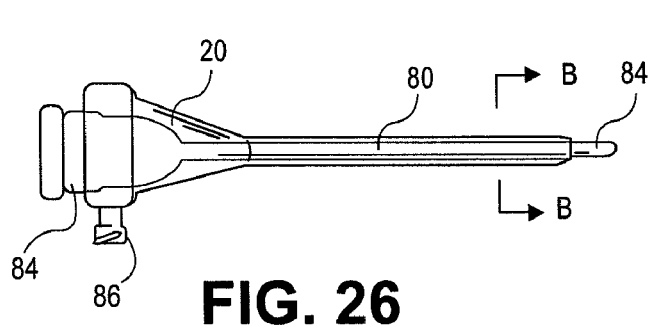
FIG. 26 is an elevational view of the access tool of FIG. 22 showing an obturator in place.

FIGS. 8 and 9 show another alternative design for the distal end of vapor delivery component 16. In addition to tear-shaped ports 40, an additional port 46 is formed in the distal tip of vapor delivery component 16. In the embodiment shown in FIG. 8A, a ball 48 is held within the distal end of vapor delivery component 16 just proximal to port 46 by a circumferential ridge 50. As vapor pressure builds within vapor delivery component 16, divots 49 in ball 48 cause it to rotate within the chamber between port 46 and ridge 50 as the pressure escapes around the partially occlusive sphere, thereby effectively closing and opening access to port 46. This motion creates puffs of vapor 52 through port 46 when ball 48 is not blocking port 46 and directs more vapor 54 out through side ports 40 when ball 48 is blocking port 46. In the embodiment shown in FIG. 8B, the movable component is a spiral wrapped elongated element 51, also held in place by ridge 50. By using a floating semi-occlusive element to raise the back-pressure at the tip of the vapor delivery component, the lumen of vapor delivery component 16 may be made larger. A larger size lumen has the advantage of reducing the amount of condensation along the course of the lumen. The amount of resistance is a function of the fit of the semi-occlusive device to the inner lumen, the amount of decrease in the ID at the ridge 50, and the presence, number and size of any fenestrations proximal to the ridge 50.

FIGS. 10-19 show details of the expansion mechanism and access tool components of a device according to one embodiment of the invention. The expansion mechanism includes a basket 18 which has two deformable arms 56 and 58 made, e.g., out of shape memory material. A two part plastic hub 60 secures the proximal ends of the basket arms and interfaces with the inner diameter of the introducer. The distal hub component 64 has keyed slots that accommodate the distal ends of the wire shafts of the basket component that allow for securing the shafts to the hub assembly locking the shafts into the keyed slots. The proximal hub component is fabricated so that it secures the shaft within the keyed slots of the distal hub component locking them in place as it is glued to the mated portion of the distal component. Lumens 66 and 68 in the first and second parts 62 and 64 of hub 60 provide access for the vapor delivery component.

FIGS. 16-20 show how the basket is loaded and delivered. In the embodiment shown in FIGS. 16-19, this can be done as is done in other medical device technologies as shown in FIGS. 17 and 18, where basket arms 56 and 58 are pulled proximally through a funnel 70 into a capture cylinder 72, and the funnel 70 is then removed. As the basket arms and capture cylinder are advanced distally through the introducer, an exterior shoulder 74 on cylinder engages a stop 92 (shown in FIG. 31) formed on the interior of the introducer just proximal to the distal end of the introducer, guides the advancement of the basket arms 56 and 58 continue to move distally. This permits arms 56 and 58 to exit the capture cylinder and expand into the uterine cavity. In the embodiment shown in FIGS. 20A and B, a metal collar 71 with a tapered inner surface 73 serves to guide the basket arms into the capture cylinder. The metal collar 71 may thereafter be left in place or removed.

Figure 27:
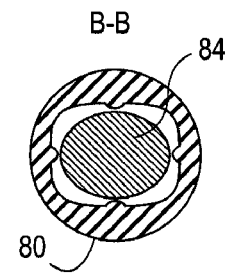
FIG. 27 is a cross-sectional view along the line B-B of FIG. 26.
Figure 28:
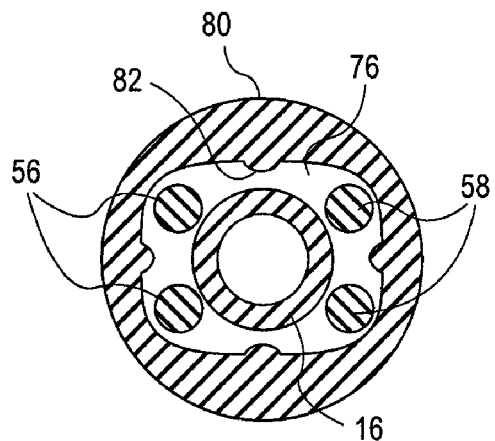
FIG. 28 is a cross-sectional view of a uterine access tool according to an embodiment of the invention.
Figure 29:
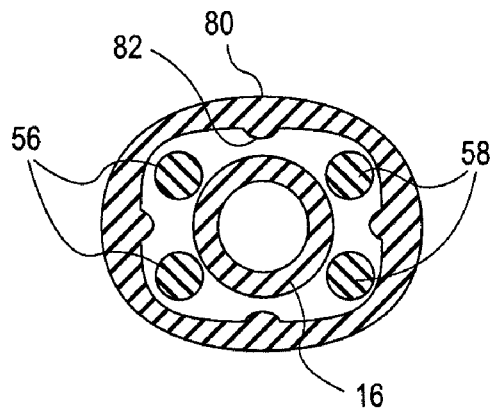
FIG. 29 is a cross-sectional view of a uterine access tool according to an embodiment of the invention.

FIGS. 21-37 show further details of the access tool or introducer. Access tool 20 has a central lumen 76 extending from an inlet 78 through a shaft 80. As shown in the cross-sectional view of FIG. 25, lumen 76 may be non-radially symmetrical in cross-section and may be formed with alignment features, such as ridges 82. The cross-sectional shape of lumen 76 and the alignment features 82 can help orient the basket arms 56 and 58 and the vapor delivery component 20 within the lumen, as shown in FIG. 28. The lumen's cross-sectional shape and alignment features may also help orient and hold an obturator 84 within the lumen 76, as shown in FIG. 27, which is placed during the introduction of the introducer at the time of the initial insertion of the device into the uterine cavity, prior to the insertion of the hysteroscope prior to the introduction of the vapor delivery component. The obturator serves to seal the distal end of the introducer as it passes through the cervix into the body of the uterus. The shaft 80 may be formed with a non-circular outer cross-sectional shape, as shown in FIG. 29, to help the user orient the device to the plane of the uterus and to decrease the outer diameter along one axis of the shaft.

Figure 30:
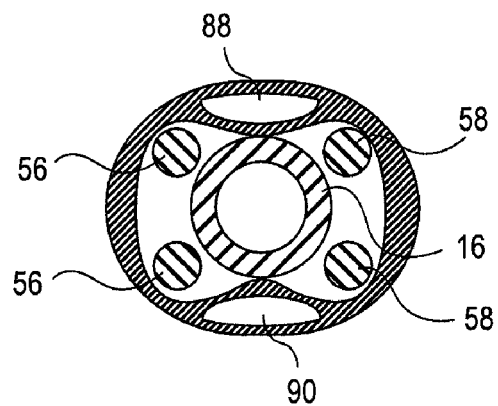
FIG. 30 is a cross-sectional view of a uterine access tool according to an embodiment of the invention along the line B-B of FIG. 31.
Figure 31:
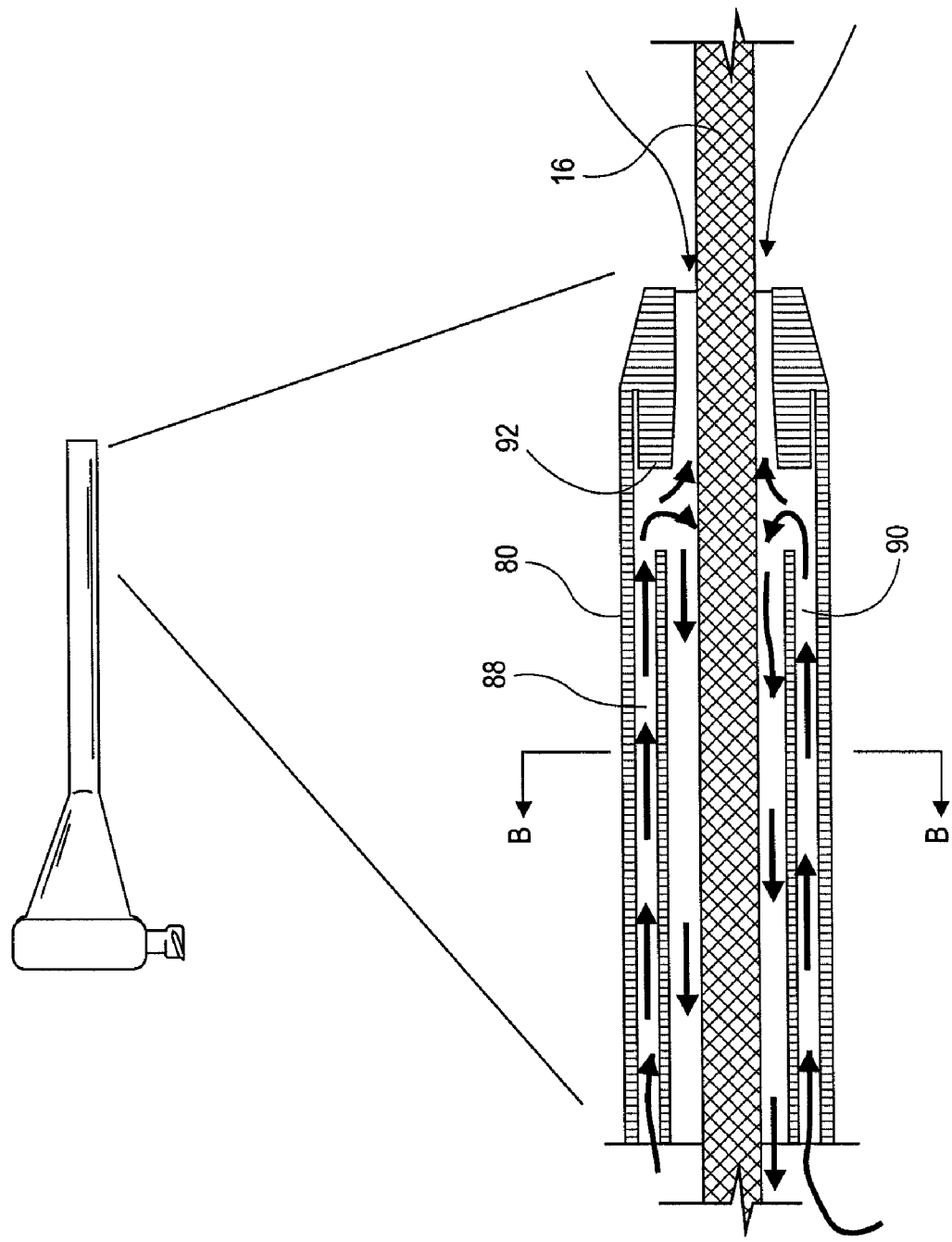
FIG. 31 is a cross-sectional view of a uterine access tool according to the embodiment of FIG. 30.

In some embodiments it may be important to minimize heat transfer to the cervical canal. As shown in FIGS. 28 and 29, the shaft of the vapor delivery component 16 is held away from the walls of the introducer by the basket arms 56 and 58 and by the alignment features 82. In some embodiments, the introducer shaft provides additional heat protection through active cooling by circulating cooling fluid around the outside of the vapor delivery component. For example, cooling fluid (such as saline) may be introduced through an inlet port 86 at the inlet of the introducer and into lumens 88 and 90 extending through the introducer shaft 80, as shown in FIGS. 30 and 31. Lumens 88 and 90 terminate proximal to the distal end of introducer shaft 80. Cooling fluid flowing out of the distal ends of lumens 88 and 90 is pushed proximally by the pressure of the vapor within the uterine cavity and flows proximally within lumen 76 around the exterior of vapor delivery component 16 and the basket arms (not shown in FIG. 31).

Figure 32:
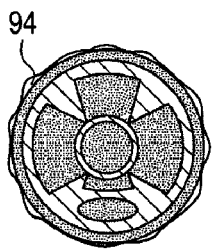
FIGS. 32-34 show cross-sectional views of alternative embodiments of uterine access tools.
Figure 33:
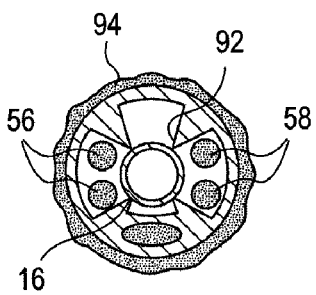
Figure 34:
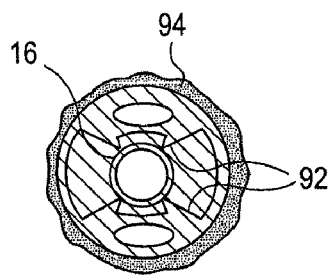

The interior introducer shaft 80 may be provided with ridges or spokes 92 to hold the vapor delivery component 16 in the center and to provide space for the basket arms 56 and 58, as shown in FIGS. 32-34. In these embodiments, introducer shaft 80 may be formed from a polyamide.

Figure 35:
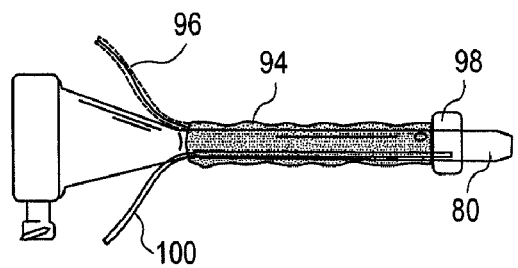
FIGS. 35 and 36 are elevational views of a uterine access tool according to yet another embodiment of the invention.
Figure 36:
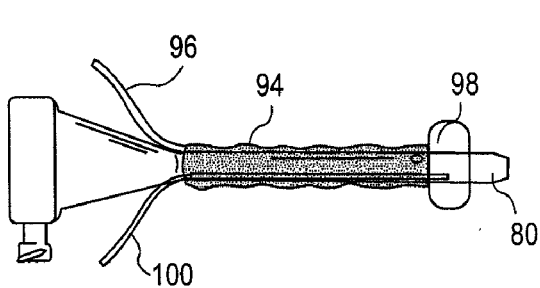
Figure 37:
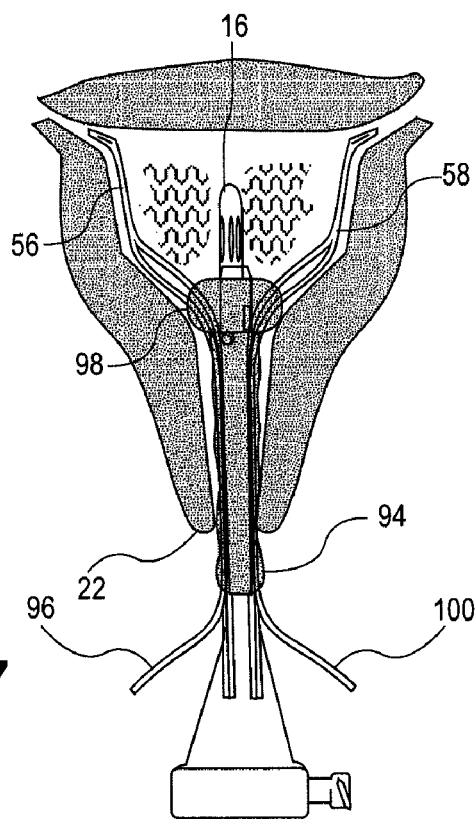
FIG. 37 shows the uterine access tool of FIGS. 35 and 36 in use with a vapor delivery tool to treat a uterus.

FIGS. 35-37 show an embodiment with an additional or alternative active cooling feature. A cooling jacket 94 is disposed around the outside of the introducer shaft. After insertion of the introducer, basket arms and the vapor delivery component into the uterus, cooling fluid may introduced into cooling jacket 94 through an inlet 96. This additional cooling will help maintain the temperature of the cervical canal within a safe range. An optional additional feature is a sealing balloon 98 around the outside of the introducer proximal to its distal end. Balloon 98 may be inflated with fluid from an inlet port 100 to seal the uterine cavity prior to introduction of vapor through vapor delivery component, as shown in FIG. 37.

Figure 38:
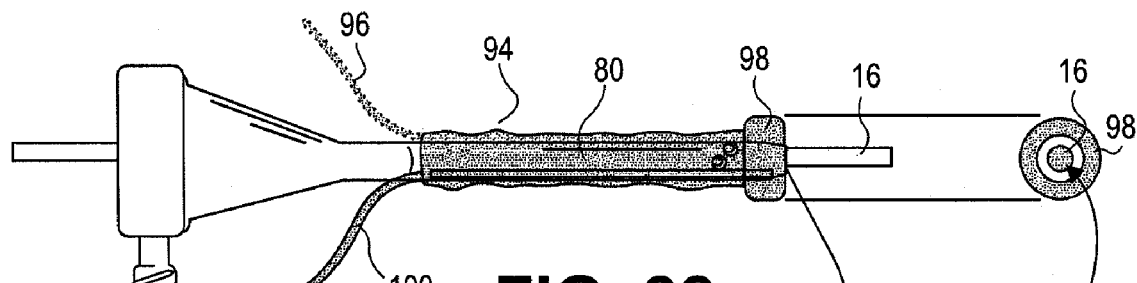
FIG. 38 are side and end elevational views of a uterine access tool and a vapor delivery tool according to still another embodiment of the invention.
Figure 39:
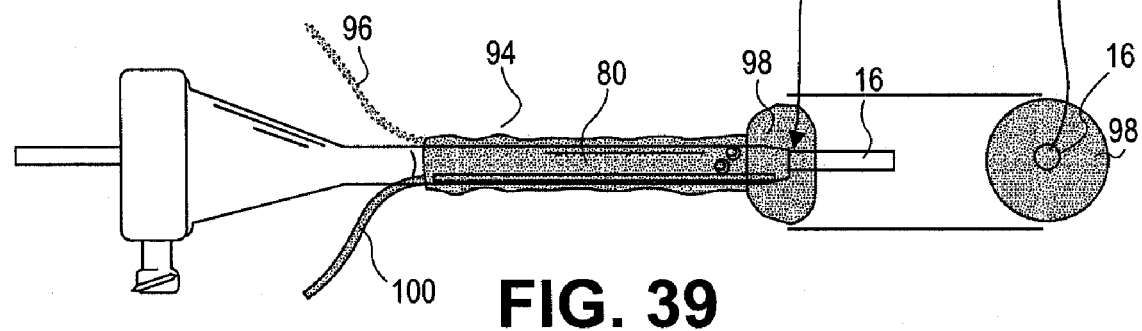
FIG. 39 are side and end elevational views of the uterine access tool and vapor delivery tool of FIG. 38.

FIGS. 38 and 39 show an embodiment in which the sealing balloon 98 is fashioned so that in the inflated state it distends beyond the distal end of the introducer shaft or cannula 80 and (as in FIG. 39) seals around the vapor delivery component 16 to occlude the fluid cooling channels of the cannula 80.

Figure 40:
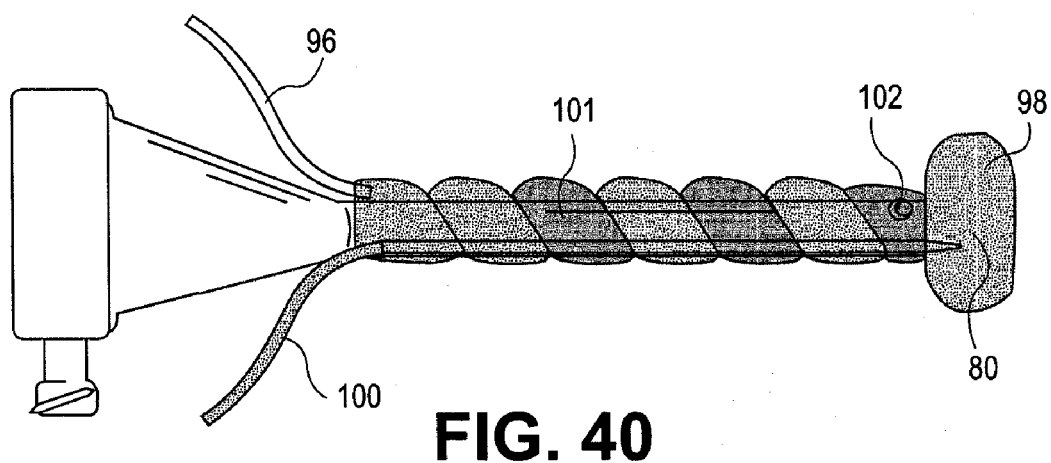
FIG. 40 is an elevational view of a uterine access tool according to yet another embodiment of the invention.
Figure 46:
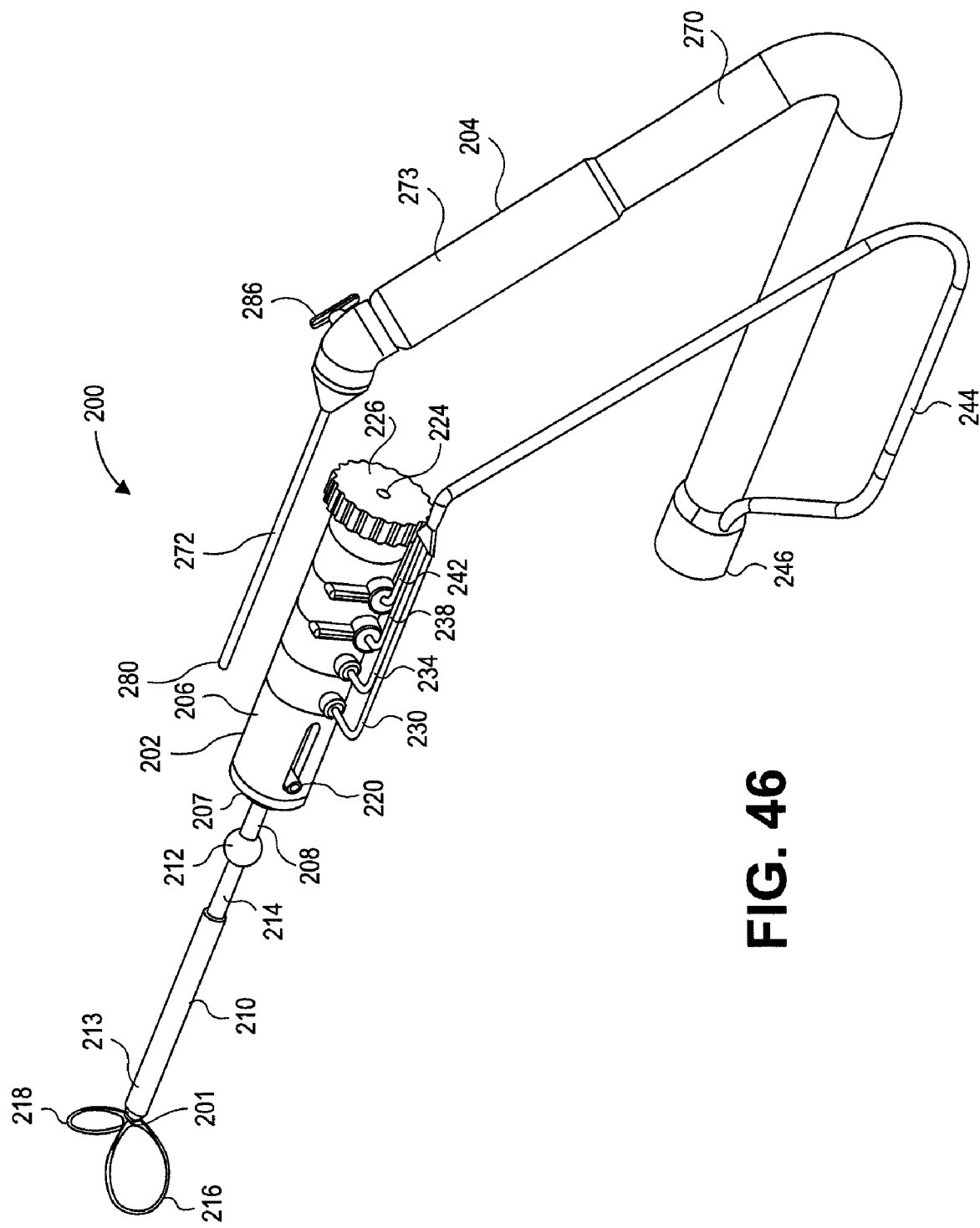
FIG. 46 is a perspective view of a uterine access tool and a vapor delivery tool according to still another embodiment of the invention.

In FIG. 40, an outer water jacket 101 (e.g., a balloon or compressible conduit, such as a PET PTCA balloon with an inner delivery component versus a guide lumen as in a PTCA balloon) wraps around delivery cannula 80. Jacket 101 surrounds the introducer in one continuous sheath or, alternatively, wraps around the introducer component spiraling from the proximal end, where the coolant inlet 96 is connected to a pressurized cold water supply. Coolant communicates with a small fenestration 102 at the distal end of the introducer that allows the coolant to leave the jacket 101 and enter the central lumen of the introducer, then travel back down the inside of the introducer lumen. When combined with the occluding distal balloon 98, this active cooling arrangement creates a circuit where there is continuous coolant flow from the outer compressible conduit to the inner cooling chamber. The flow is a function of the inlet pressure of the coolant and the size of the fenestration in the introducer that provides resistance to the pressurized coolant before allowing it to flow into the central chamber. The coolant source can be, e.g., a transfusion pressure bag or an IV bag as used in blood transfusions. The coolant pressurizes the outer conduit so that it inflates over the tissue interface, thereby separating the tissues being protected from the thermal source with a flowing coolant component.

An alternative active cooling arrangement is to have the return of the coolant travel within a second compressible spiraling conduit running along side of the first conduit like a candy cane where one helical stripe flows in one direction proximal to distal and the other helical stripe flows distal to proximal. These conduits communicate at the distal end to complete the return path rerouting the coolant back down the shaft on the outside of the shaft instead of via the inner lumen. There could also be a temperature feedback mechanism within the conduit so that flow can be increased in response to a rise in temperature.

FIGS. 41-42 show an embodiment in which the vapor delivery component 16 has an inner lumen 108 surrounded by an outer, sealed lumen 104. Inner lumen 108 is held away from the walls of outer lumen 104 by spacers 106. A vacuum may be formed in outer lumen 108 to insulate the inner lumen.

FIG. 43 shows an embodiment in which the delivery cannula 80 has a plurality of longitudinal spokes or spacers 110 projecting radially inward and holding the vapor delivery component 16 (or other device) centered within the lumen. Coolant may flow through channels 112. Spokes 110 may have sharp tips to reduce the mass coming into contact with the hot vapor delivery component. The remainder of each spoke serves as a heat exchanger to transfer heat from the spoke tip to the coolant.

FIGS. 44 and 45 show a modification to the FIG. 43 embodiment in which the spokes 110 are scalloped to further reduce the points of contact between the vapor delivery component 16 and the delivery cannula material. The scalloping also increases the contact between the flowing coolant and the hot vapor delivery component.

FIGS. 46-52 show yet another embodiment of a uterine heat therapy system 200. The main components of system 200 are a uterine access tool 202, a vapor probe 204 and a vapor source or generator (not shown). Access tool 202 has a handle 206 with an access cannula 208 extending distally from the distal end 207 of the handle 206. A sealing balloon 210 surrounds the distal portion of the cannula 208 and extends proximally to an indicator balloon segment 212. The distal end 201 of cannula 208 may be blunt or rounded to serve as an obturator during insertion of the access tool into a patient's uterus.

In this embodiment, the distal portion 213 of the balloon has a uniform diameter, and an optional intermediate stepped portion 214 is formed in the balloon. In alternative embodiments, the stepped portion may be eliminated, and/or an increased diameter balloon portion may be formed at the distal end of the balloon. In addition, the indicator portion may optionally be a separate member in alternative embodiments. The balloon 210 is shown in its inflated state in FIGS. 46 and 47. During insertion into the uterus, the balloon will be in a flattened or deflated state to lower the access tool's insertion profile.

As in earlier embodiments, access tool 202 has an expansion mechanism for moving uterine tissue apart and away from the tool. In this embodiment, the expansion mechanism has two flexible arms 216 and 218 formed, e.g., from shape memory material. Arms 216 and 218 are integral with or connected to wires or rods extending proximally through access tool 202 along or within cannula 208 to an actuator 220 on handle 206. In this embodiment, the wires extending proximally from arms 216 and 218 are disposed in lumens 217 and 219 formed in cannula 208. The lumens 217 and 219 are shown in FIGS. 49 and 50, which omit the wires for clarity.

Figure 47:
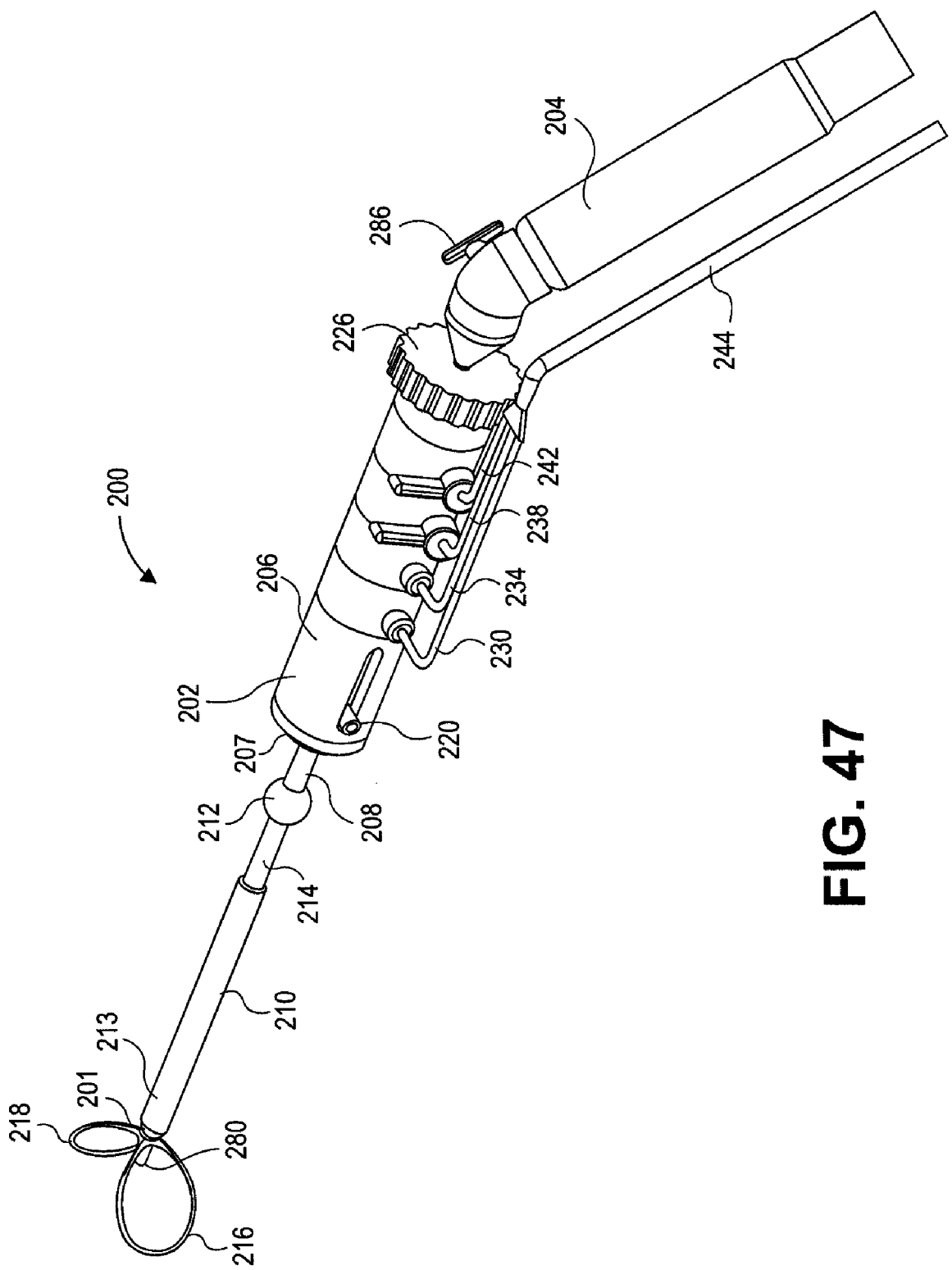
FIG. 47 is a perspective view of the embodiment of FIG. 46 with the vapor delivery tool inserted into the uterine access tool.
Figure 48:
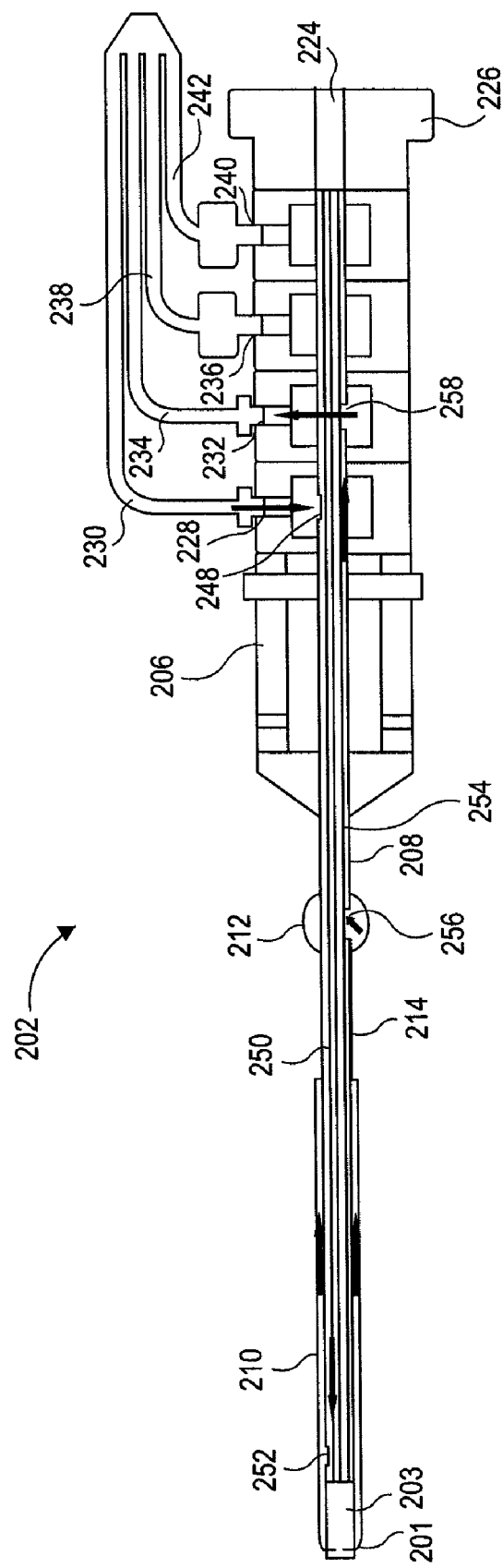
FIG. 48 is a cross-sectional view of the uterine access tool of FIG. 46.

Actuator 220 may be operated to advance or withdraw arms 216 and 218, which are shown in their advanced state in FIGS. 47 and 48. In this advanced stated within a uterus, arms 216 and 218 move uterine tissue away from the distal end of access tool 202. Unlike earlier embodiments, however, arms 216 and 218 extend only partway up the uterine wall and do not reach or occlude either fallopian tube os. When withdrawn, arms 216 and 218 collapse and are pulled into a chamber 203 formed in the distal portion of cannula 208.

Figure 49:
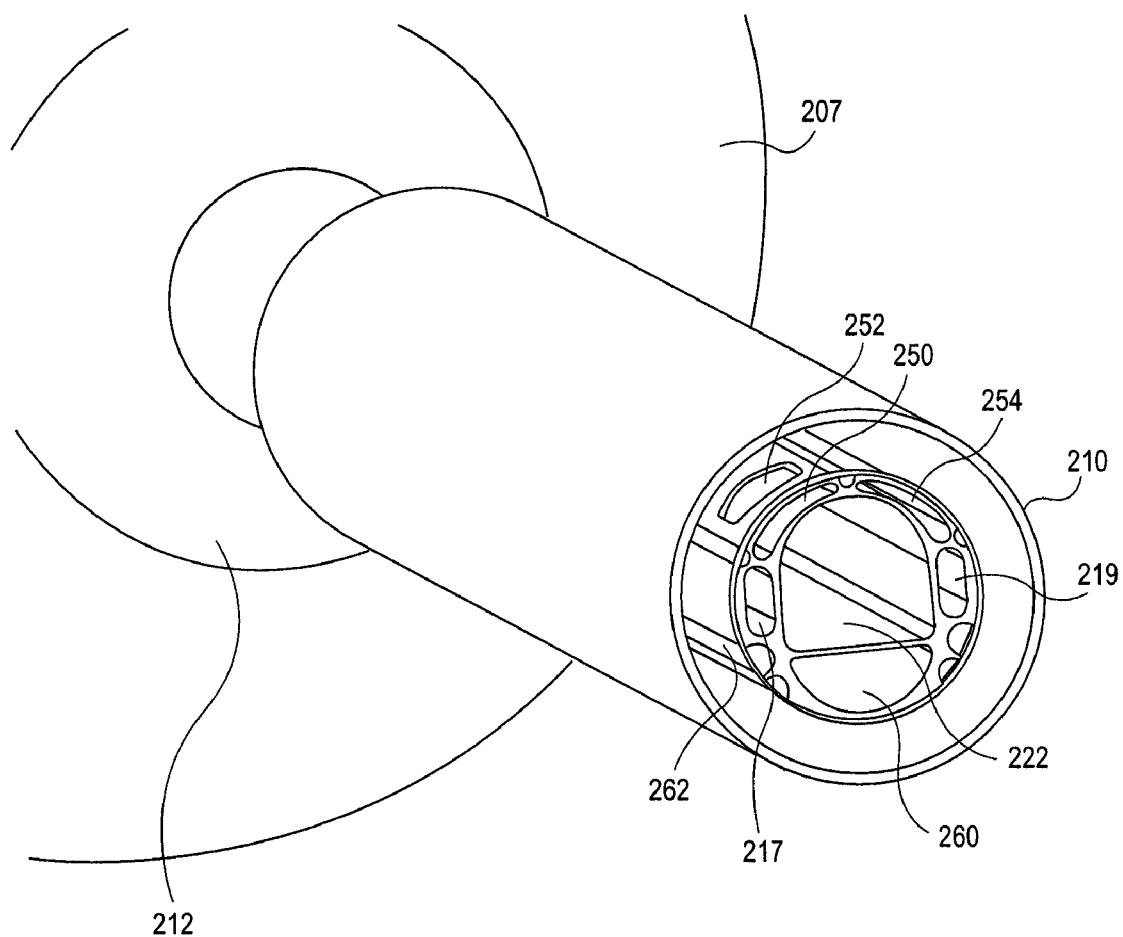
FIG. 49 is a cross-sectional view of the uterine access tool of FIG. 46.
Figure 50:
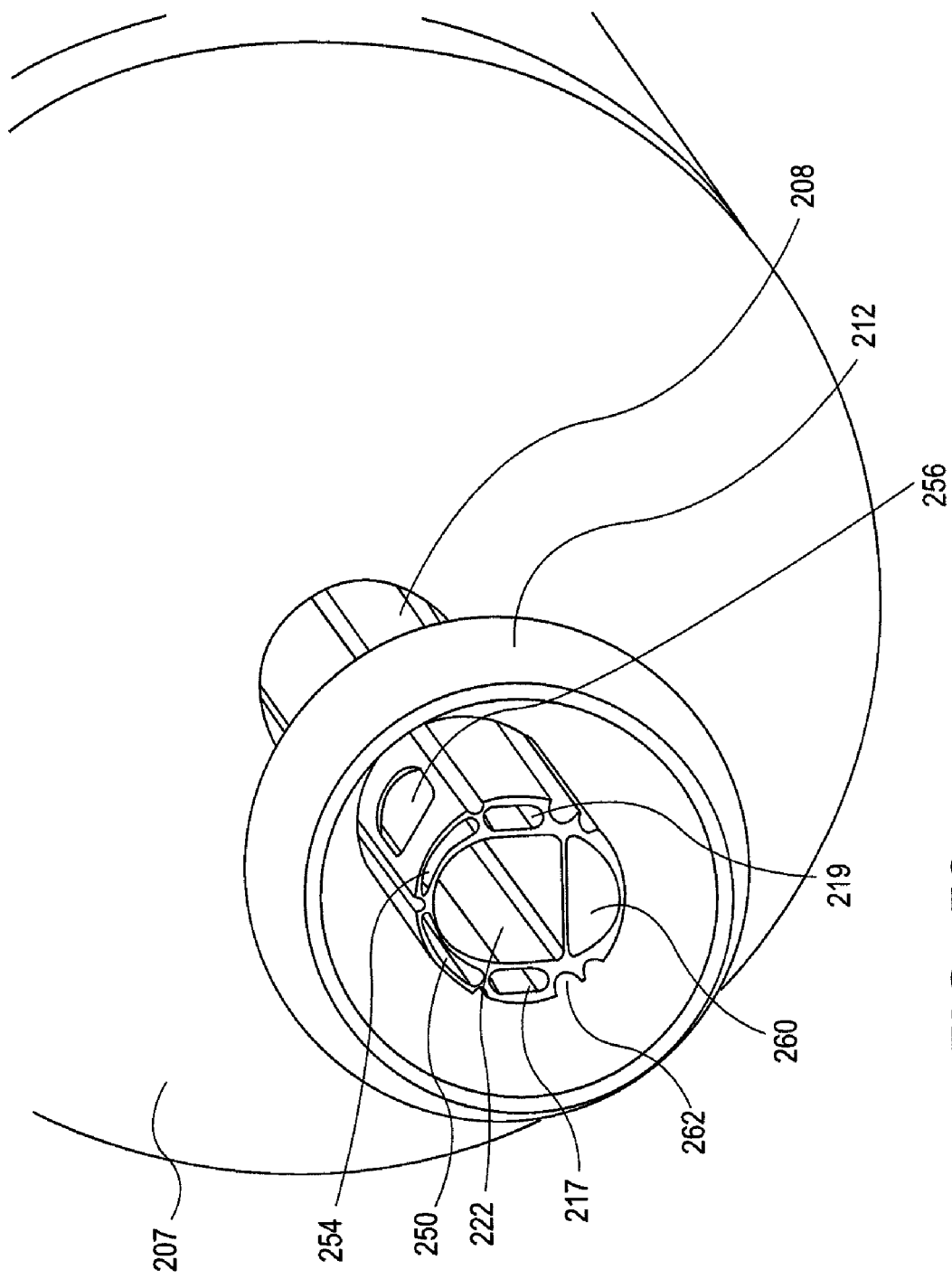
FIG. 50 is another cross-sectional view of the uterine access tool of FIG. 46.

As shown in more detail in FIGS. 48-50, cannula 208 has a plurality of lumens. A central access lumen 222 communicates at its proximal end with a port 224 in a Tuohy-Borst clamp 226. At its distal end, lumen 222 extends to the distal end of the cannula and into the uterus when the access tool is placed in the uterus. A port at the distal end of lumen 222 and in the proximal portion of chamber 203 is disposed between the arms 216 and 218 of the expansion mechanism.

A plurality of inlet and outlet ports are formed in handle 206. A coolant inlet port 228 connects to a coolant inlet line 230; a coolant outlet port 232 connects to a coolant outlet line 234; a saline flush inlet port 236 connects to a saline inlet line 238; and a saline outlet port 240 connects to a saline outlet line 242. In this embodiment, the inlet and outlet lines combine into an optional single flexible hose 244. Hose 244 connects to sources of coolant and saline flush solution (not shown) via a connector 246.

As shown in FIGS. 48-50, coolant entering handle 206 through port 228 enters cannula lumen 250 via an opening 248 formed in the proximal end of cannula 208 within handle 206. A port 252 formed in a distal portion of lumen 250 allows coolant to exit the lumen and enter the interior of balloon 210. The pressurized coolant flows proximally within balloon 210 and enters a return lumen 254 through a port 256 located within the indicator portion 212 of the balloon. The returning coolant exits lumen 254 via an opening 258 in the handle and then enters coolant return line 234 through port 232. This flow path is shown by arrows in FIG. 48.

In a similar manner, pressurized saline may be introduced through inlet line 238 and port 236 which communicates with lumen 222 via an opening (not shown) within handle 206 so that the uterus can be flushed with saline. Returning saline from the uterus enters a lumen 260 in cannula 208, then flows back through an opening (not shown) within handle 206, then through port 240 into return line 242.

Cannula 208 may be formed with optional longitudinal grooves 262 to provide a return flow path for the coolant through the balloon, even if the patient's anatomy does not permit the balloon to inflate in any substantial way.

Figure 51:
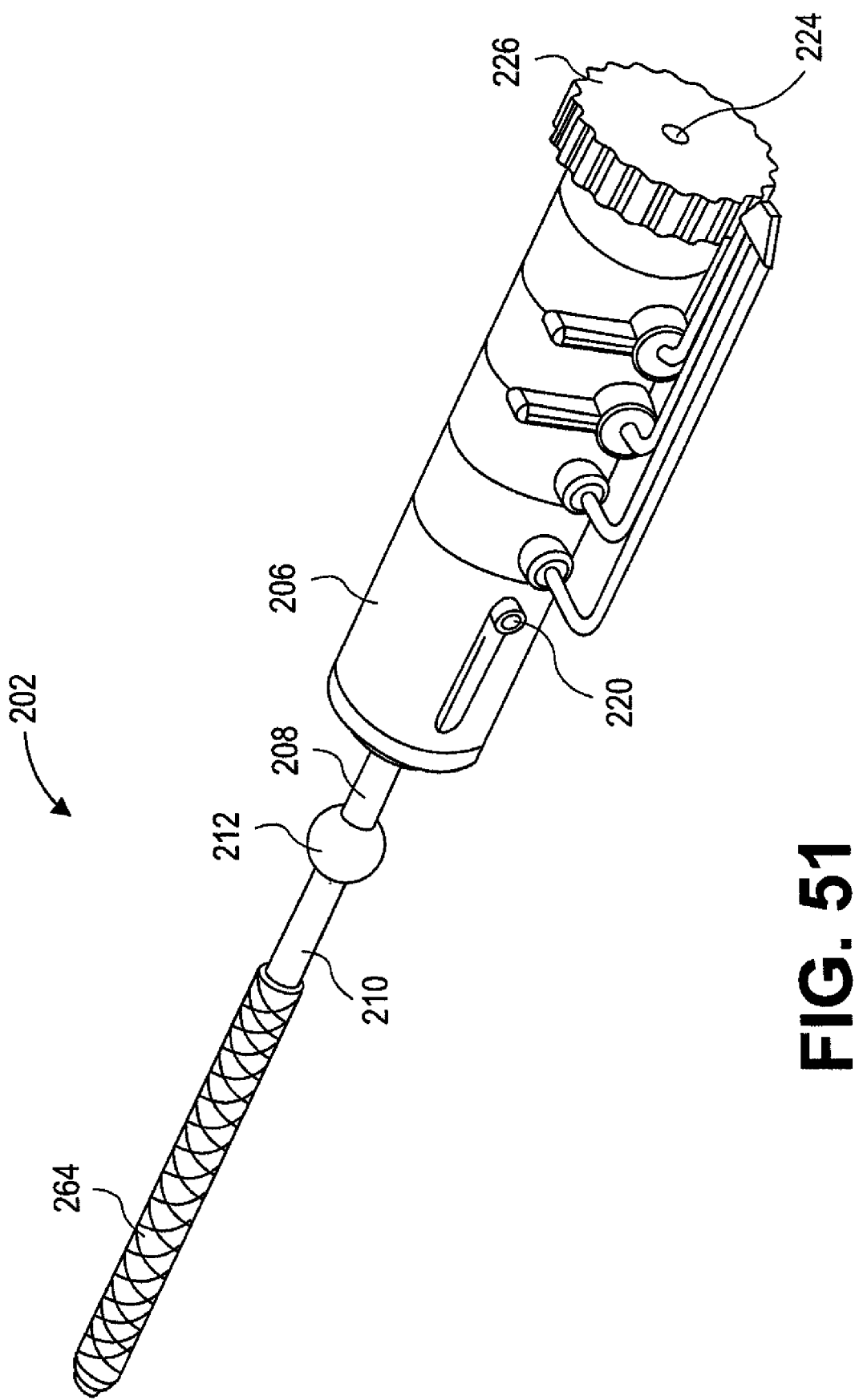
FIG. 51 is a perspective view of a uterine access tool according to another embodiment of the invention.

FIG. 51 shows an optional mesh or net 264 covering at least a distal portion of balloon 210 to constrain expansion of that portion of the balloon. Also in FIG. 51, the expansion mechanism actuator 220 has been moved to draw the expansion arms into the distal end of the access tool.

Figure 52:
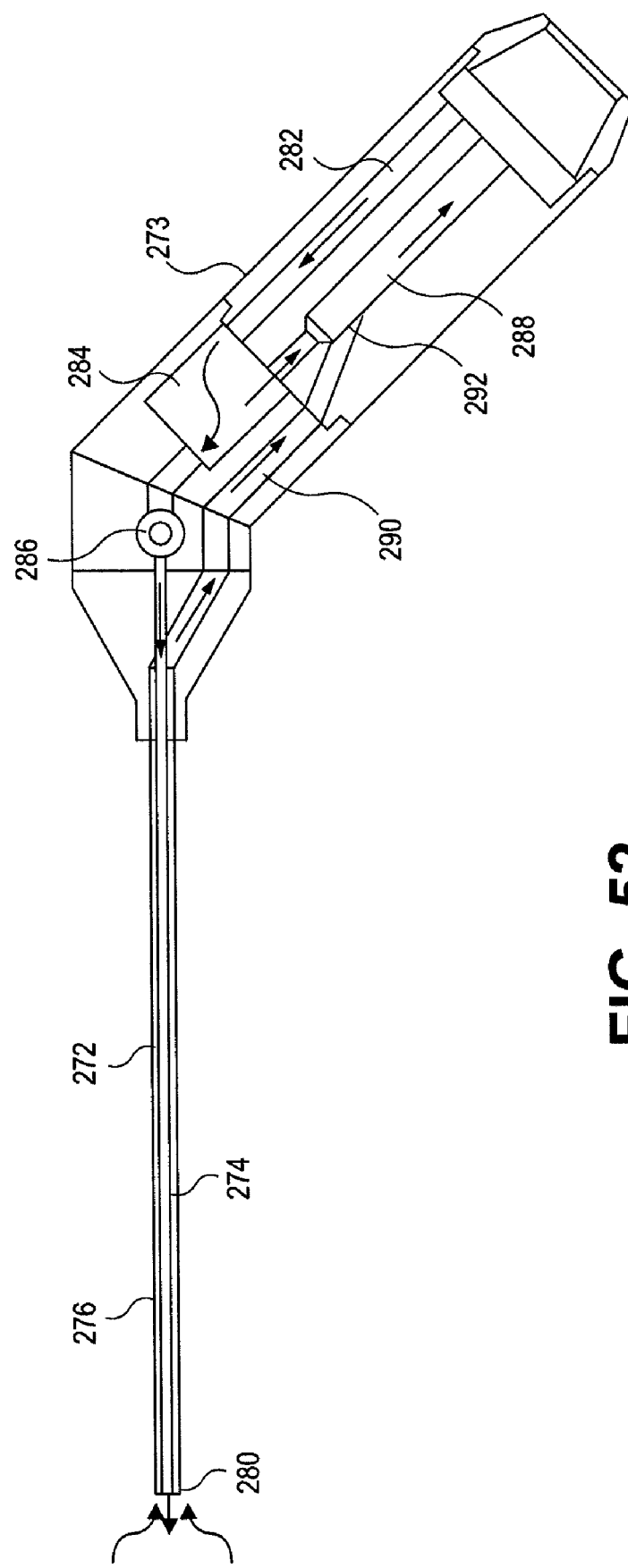
FIG. 52 is a cross-sectional view of the vapor delivery tool of FIG. 46.

Vapor probe 204 connects to a vapor source (not shown), such as a boiler or other steam generator, via an insulated flexible hose 270 and connector 246. A vapor delivery cannula 272 extending from a handle 273 has a central vapor delivery lumen 274 and a concentric annular vapor return lumen 276 surrounding lumen 274, as shown in FIG. 52. When inserted through port 224 into lumen 222 of the access cannula 208, the distal end 280 of vapor delivery cannula 272 extends beyond the distal end of cannula 208 to a position between expansion arms 216 and 218 when the arms are in their advanced position, as shown in FIG. 47.

When connected to a vapor source, vapor flows through a vapor supply lumen (not shown) in hose 270 into handle 273 through a lumen 282 into a chamber 284. When valve 286 is in its closed position, all vapor entering chamber 284 flows through a lumen 288 back into a vapor exhaust lumen (not shown) in hose 270 to a vapor and/or condensate collection vessel (not shown). This flow of vapor within the handle portion of the vapor probe provides a warming circuit for the vapor probe to help ensure that the vapor quality will be maintained at its appropriate level when the valve is opened and vapor is delivered to the patient.

When valve 286 is opened, at least a portion of the vapor flows through valve 286 into lumen 274 of vapor cannula 272 and out the distal end of the vapor cannula for providing uterine heat therapy. Returning vapor and/or condensate flows proximally through annular lumen 276 into a vapor return lumen 290 in handle 273, then through an opening 292 into lumen 288 and the vapor exhaust lumen in hose 270. Vapor flow is shown by arrows in FIG. 52.

In one embodiment, only a portion of the vapor supplied to chamber 284 of the vapor probe flows into vapor delivery cannula 272 when valve 286 is open. In this embodiment, most of the vapor returns through lumen 288 to hose 270. Vapor flowing in lumen 288 past the opening 292 of vapor return lumen provides a venturi action that helps pull the exhaust vapor and any condensate through lumen 290 and annular lumen 276.

A thermocouple (not shown) may be disposed at the distal end of the vapor delivery cannula 272 and connected to a monitor or controller (not shown) to monitor intrauterine temperature and provide a signal to a vapor delivery controller for controlling the therapy.

When using the system of the invention to provide uterine heat therapy to a patient to treat, e.g., endometriosis, access to the uterus is obtained by inserting a speculum into the patient's vagina and grasping the cervix with a tenaculum. The tenaculum pulls the cervix forward while the speculum pushes down on the patient's peritoneum to straighten the uterine canal and align it with the vaginal canal. If desired, a hysteroscope may be inserted through port 224 of the access tool with the distal end of the hysteroscope at the level of the obturator tip 201 of the access tool, and the Tuohy-Borst seal may be tightened around the hysteroscope. The access tool cannula may then be lubricated and inserted through the cervix. The flexibility of the access tool (including the flexible cannula 208 and flexible expansion arms 216 and 218) permits insertion with a minimum of straightening of the cervical canal. In addition, the blunt obturator tip 201 of the access cannula 208 helps minimize the likelihood of perforation as the access tool is advanced.

Once the distal end of the access cannula 208 has passed through the internal cervical os into the uterine cavity, the hysteroscope can be used to confirm placement. The hysteroscope may be advanced beyond the distal end of the access cannula 208, if desired. After confirming position of the access cannula, the expansion arms 216 and 218 are advanced by pushing actuator 220 forward. This action engages arms 216 and 218 with the uterine wall tissue to move the tissue away from the distal end of the vapor probe.

The coolant balloon 210 may then be inflated by providing pressurized coolant through the coolant inlet, as described above. Balloon 210 expands to seal the cervical canal up to the internal cervical os. As the balloon engages the cervical canal wall, coolant pressure will continue to rise up toward the coolant inlet pressure. When the pressure of coolant within the balloon reaches an indicator pressure, the indicator portion 212 of the balloon will expand to provide an indication to the user that the distal portion of the balloon has engaged the wall of the cervical canal to seal the opening. If a hysteroscope was used, it can now be removed.

The vapor delivery cannula 272 of vapor probe 204 is then inserted through port 224 until the distal tip 280 extends through the distal end of the access cannula 208, as shown in FIG. 47. Hose 270 may be connected to the vapor source prior to or while the access tool is being inserted into the patient so that the warming circuit can warm the vapor probe handle and internal components. When ready to deliver therapy to the patient, valve 286 is opened to permit vapor to flow through vapor delivery cannula 272 into the patient's uterus.

In one embodiment, a thermocouple disposed at the distal end of the vapor delivery cannula monitors intrauterine temperature. The thermocouple provides a temperature signal to a vapor delivery controller to initiate a timed sequence once the uterine cavity reaches a threshold temperature, such as 50° C. The controller discontinues vapor flow after the predetermined time.

After completion of the vapor therapy, the expansion arms are retracted and coolant flow is stopped. After the indicator balloon segment deflates, the access tool and vapor delivery probe may be removed from the patient.

In some embodiments of the method, a saline flush may be provided prior to the procedure and/or at the end of the procedure. As described above, saline may be provided through lumen 222 around the hysteroscope or vapor delivery probe. Delivering saline at the end of the procedure may be desirable to release any vacuum formed in the uterus due to condensation of vapor.

Vapor may be delivered to the uterus at an intrauterine pressure of 5 to 35 mm Hg. Coolant pressure within the sealing balloon may be 50 to 300 mm Hg. Typical therapy time for treating endometrial tissue may range from 15 sec. to 120 sec., with a preferred duration of 45-60 sec.

FIGS. 53-55 show another embodiment of the uterine heat therapy system of this invention. In this embodiment, the distal end of an expansion mechanism 302 extends beyond the distal end of a uterine access tool cannula 304. Expansion mechanism 302 has two blunt distal ends 306 and 308 each of which has aproximally facing shoulder 310 and 312, respectively. Shoulders 310 and 312 rest on the distal end 316 of cannula 304 when the expansion mechanism is in its undeployed position, as shown in FIG. 53B.

A central fenestration channel is formed by the cooperation of two half channels 318 and 320 formed on cooperating interior surfaces 319 and 321 of expansion mechanism ends 306 and 308 to provide an opening through the expansion mechanism, even in its undeployed position, to permit access through the expansion mechanism by a hysteroscope or probe 322 as shown in FIG. 53A. The channel may be used to permit visualization by a hysteroscope during advancement of the access tool into the uterus.

Actuation wires or rods 324 extend proximally from the distal ends of the expansion mechanism through an interior lumen 326 of the cannula to an actuator (not shown). Other lumens 328 may be formed in cannula 304 for coolant flow, saline flush, etc. as described in earlier embodiments.

When the expansion mechanism is actuated, the distal ends 306 and 308 move distally. As the ends 306 and 308 move distally, camming surface 330 on distal end 306 and camming surface 332 on distal end 308 slide against the hysteroscope (or other inserted component) 322, and camming surface 334 on distal end 306 and camming surface 336 on distal end 308 slide against the distal end of cannula 304 to cause the distal ends 306 and 308 to move apart, thereby engaging and moving uterine tissue away from the distal end of the inserted tool 322, as shown in FIG. 54. Further distal advancement of the expansion mechanism causes the distal ends 306 and 308 to move further apart due to a pre-bent shape of the wires or rods 324, as shown in FIG. 55.

Figure 56:
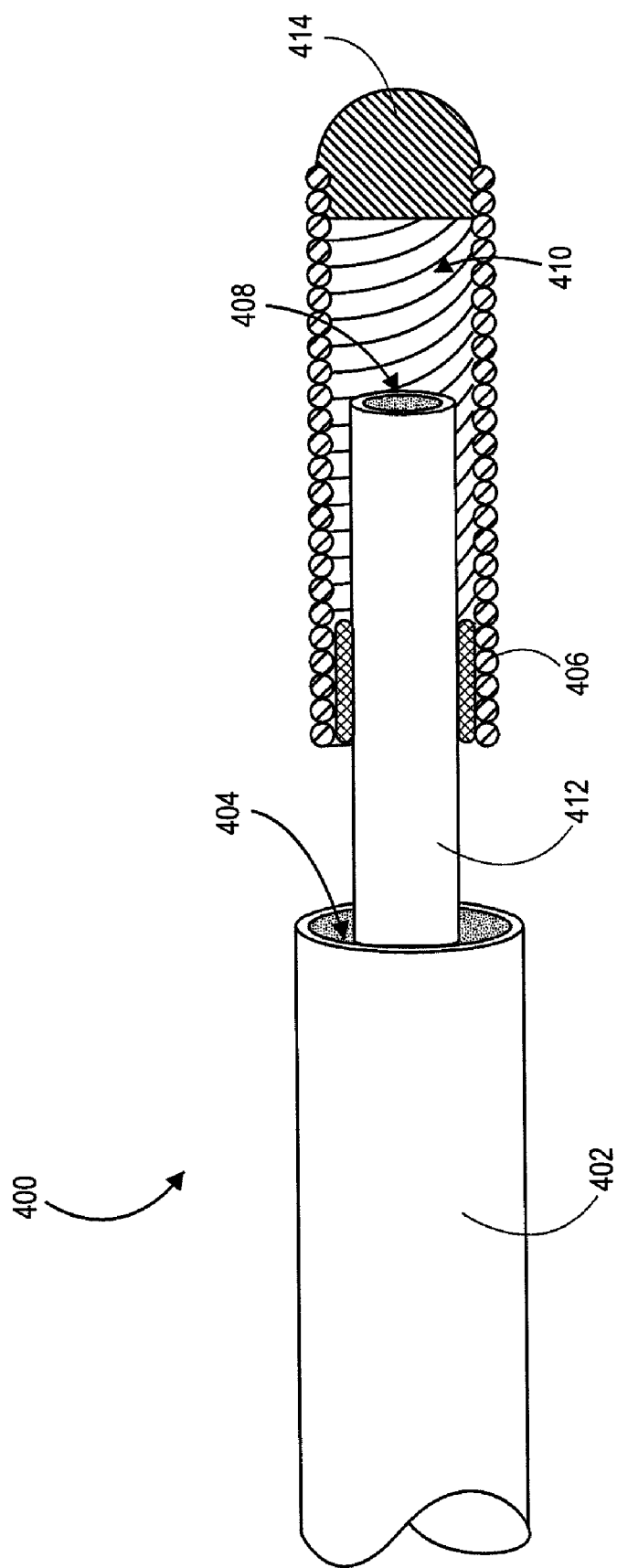
FIG. 56 is a perspective and partial cross-sectional view of a uterine therapy system according to yet another embodiment of the invention.

FIG. 56 shows aspects of a uterine therapy system 400 according to yet another embodiment of the invention. In this embodiment, the distal end 408 of the vapor delivery probe 412 extends beyond the distal end 404 of the uterine access tool cannula 402. During therapy, vapor is delivered from the distal end of the vapor delivery probe 412, and vapor and/or condensate is returned through the annular space in the cannula surrounding the vapor delivery probe.

An atraumatic tip 414 is supported distal to the distal end of the vapor delivery probe by a coil 410. Coil 410 may be attached to the probe 412 by, e.g. welding. During vapor delivery, vapor will pass through adjacent windings of coil 410 to reach uterine tissue.

What is claimed is:

1. A method of providing heat therapy to a patient's uterus comprising:
   inserting an access tool through a cervix and a cervical canal into the uterus, the access tool comprising a lumen;
   after inserting the access tool into the uterus, creating a seal between an exterior surface of the access tool and an interior cervical os;
   providing an indication to a user that the seal has been created;
   delivering vapor through the access tool lumen into the uterus; and
   condensing the vapor on tissue within the uterus.

2. The method of claim 1 wherein the step of creating a seal comprises expanding an expandable member.

3. The method of claim 2 wherein the expandable member comprises a balloon.

4. The method of claim 3 wherein the expanding step comprises preferentially expanding a sealing portion of the balloon disposed at the interior cervical os prior to an indicator portion of the balloon disposed proximal to the interior cervical os.

5. The method of claim 1 further comprising placing an expansion mechanism in contact with tissue within the uterus to move uterine tissue away from an opening in the access tool lumen.

6. The method of claim 5 further comprising advancing the expansion mechanism distally with respect to the access tool lumen prior to the placing step.

7. The method of claim 1 wherein the step of delivering vapor comprises inserting a vapor delivery tool through the access tool lumen.

8. The method of claim 1 further comprising exhausting vapor and/or vapor condensate from the uterus.

9. A method of providing heat therapy to a patient's uterus comprising:
   inserting an access tool through a cervix and a cervical canal into the uterus, the access tool comprising a lumen;
   after inserting the access tool into the uterus, expanding a balloon to create a seal between an exterior surface of the access tool and an interior cervical os, wherein expanding comprises preferentially supplying coolant to a sealing portion of the balloon disposed at the interior cervical os prior to supplying coolant to an indicator portion of the balloon disposed proximal to the interior cervical os;
   providing an indication to a user that the seal has been created;
   delivering vapor through the access tool lumen into the uterus; and
   condensing the vapor on tissue within the uterus.

* * * * *